(12) United States Patent
Iijima et al.

(10) Patent No.: US 9,017,957 B2
(45) Date of Patent: Apr. 28, 2015

(54) PROSTASIN PARTIAL PEPTIDE AND ANTI-PROSTASIN ANTIBODY

(75) Inventors: Hiromi Iijima, Ibaraki (JP); Noriya Ohta, Ibaraki (JP); Kimio Tomita, Kumamoto (JP); Kenichiro Kitamura, Kumamoto (JP)

(73) Assignees: Hitachi Chemical Company, Ltd., Tokyo (JP); Kimio Tomita, Kumamoto (JP); Kenichiro Kitamura, Kumamoto (JP)

( * ) Notice: Subject to any disclaimer, the term of this patent is extended or adjusted under 35 U.S.C. 154(b) by 999 days.

(21) Appl. No.: 12/226,905

(22) PCT Filed: May 1, 2007

(86) PCT No.: PCT/JP2007/059790
§ 371 (c)(1),
(2), (4) Date: Oct. 31, 2008

(87) PCT Pub. No.: WO2007/126160
PCT Pub. Date: Nov. 8, 2007

(65) Prior Publication Data
US 2009/0170126 A1 Jul. 2, 2009

(30) Foreign Application Priority Data
May 1, 2006 (JP) .................................. 2006-127575

(51) Int. Cl.
| G01N 33/53 | (2006.01) |
| G01N 33/531 | (2006.01) |
| G01N 33/534 | (2006.01) |
| G01N 33/535 | (2006.01) |
| G01N 33/536 | (2006.01) |
| G01N 33/537 | (2006.01) |
| G01N 33/573 | (2006.01) |
| G01N 33/574 | (2006.01) |
| G01N 33/577 | (2006.01) |
| C07K 7/08 | (2006.01) |
| C07K 14/47 | (2006.01) |
| C07K 16/18 | (2006.01) |
| C07K 16/40 | (2006.01) |
| C07K 16/28 | (2006.01) |
| C12N 9/64 | (2006.01) |
| G01N 33/68 | (2006.01) |

(52) U.S. Cl.
CPC ................. *C07K 16/40* (2013.01); *C07K 16/28* (2013.01); *C12N 9/6424* (2013.01); *G01N 33/57484* (2013.01); *G01N 33/6893* (2013.01); *G01N 2333/96441* (2013.01); *G01N 2800/321* (2013.01); *Y10S 436/811* (2013.01); *Y10S 436/813* (2013.01)

(58) Field of Classification Search
None
See application file for complete search history.

(56) References Cited

U.S. PATENT DOCUMENTS
2002/0039753 A1  4/2002 Chai et al.

OTHER PUBLICATIONS

Yu et al (Journal of Biological Chemistry, 1994, vol. 269, pp. 18843-18484).*
Z. Tong et al., "Prostasin, a membrane-anchored serine peptidase, regulates sodium currents in JME/CF15 cells, a cystic fibrosis airway epithelial cell line", Am J Physiol Lung Cell Mol Physiol 287: L928-L935, Jun. 2004.
S. Mok et al., "Prostasin, a Potential Serum Marker for Ovarian Cancer: Identification Through Microarray Technology", Journal of National Cancer Institute, vol. 93, No. 19, Oct. 3, 2001.
Extended European Search Report dated Sep. 17, 2010, including Supplementary European Search Report and European Search Opinion, for EP Application No. 07743225.0-2405/2020417 PCT/JP2007059790.
J. X. Yu, et al., "Molecular Cloning, Tissue-specific Expression, and Cellular Localization of Human Prostasin mRNA (*)", *Journal of Biological Chemistry*, vol. 270, No. 22, Jun. 2, 1995, pp. 13483-13489.
L. M. Chen, et al., "Prostasin Is a Glycosylphosphatidylinositol-anchored Active Serine Protease*" *The Journal of Biological Chemistry*, vol. 276, No. 24, Jun. 15, 2001, pp. 21434-21442.

* cited by examiner

*Primary Examiner* — Karen Canella
(74) *Attorney, Agent, or Firm* — Antonelli, Terry, Stout & Kraus, LLP

(57) ABSTRACT

An object of the present invention is to provide an antibody that can be stably supplied and can react with prostasin under non-denaturation and denaturation conditions, and an antigen peptide for preparation of the antibody. The present invention relates to a peptide consisting of the amino acid sequence shown in SEQ ID NO: 1 or a peptide consisting of an amino acid sequence that has a deletion, a substitution, or an addition of one or several amino acids with respect to the amino acid sequence shown in SEQ ID NO: 1 and having antigenicity of prostasin. Furthermore, the present invention relates to an antibody prepared using the peptide as an antigen.

34 Claims, 12 Drawing Sheets
(1 of 12 Drawing Sheet(s) Filed in Color)

A

B

SEQUENCE LISTING

```
<160> NUMBER OF SEQ ID NOS: 10

<210> SEQ ID NO 1
<211> LENGTH: 19
<212> TYPE: PRT
<213> ORGANISM: Artificial
<220> FEATURE:
<223> OTHER INFORMATION: synthetic peptide

<400> SEQUENCE: 1

Ala His Gln Leu Asp Ser Tyr Ser Glu Asp Ala Lys Val Ser Thr Leu
1               5                   10                  15

Lys Asp Ile

<210> SEQ ID NO 2
<211> LENGTH: 1834
<212> TYPE: DNA
<213> ORGANISM: Homo sapiens
<220> FEATURE:
<221> NAME/KEY: CDS
<222> LOCATION: (229)..(1257)
<223> OTHER INFORMATION:
<220> FEATURE:
<221> NAME/KEY: mat_peptide
<222> LOCATION: (325)..(1257)
<223> OTHER INFORMATION:
<220> FEATURE:
<221> NAME/KEY: misc_feature
<222> LOCATION: (361)..(1080)
<223> OTHER INFORMATION: serine protease
<220> FEATURE:
<221> NAME/KEY: sig_peptide
<222> LOCATION: (229)..(324)
<223> OTHER INFORMATION:

<400> SEQUENCE: 2
agacggtgct ggtgactcgt ccacactgct cgcttcggat actccaggcg tctcccgttg      60
cggccgctcc ctgccttaga ggccagcctt ggacacttgc tgccctttc cagcccggat     120
```

-continued

```
tctgggatcc ttccctctga gccaacatct gggtcctgcc ttcgacacca ccccaaggct      180
tcctaccttg cgtgcctgga gtctgcccca ggggcccttg tcctggcc atg gcc cag       237
                                                     Met Ala Gln
                                                            -30 aag ggg gtc ctg ggg cct ggg cag ctg ggg gct gtg gcc att ctg ctc        285
Lys Gly Val Leu Gly Pro Gly Gln Leu Gly Ala Val Ala Ile Leu Leu
            -25                 -20                 -15 tat ctt gga tta ctc cgg tcg ggg aca gga gcg aaa ggg gca gaa gct        333
Tyr Leu Gly Leu Leu Arg Ser Gly Thr Gly Ala Glu Gly Ala Glu Ala
            -10                  -5                 -1   1 ccc tgc ggt gtg gcc ccc caa gca cgc atc aca ggt ggc agc agt gca        381
Pro Cys Gly Val Ala Pro Gln Ala Arg Ile Thr Gly Gly Ser Ser Ala
      5                  10                  15 gtc gcc ggt cag tgg ccc tgg cag gtc agc atc acc tat gaa ggc gtc        429
Val Ala Gly Gln Trp Pro Trp Gln Val Ser Ile Thr Tyr Glu Gly Val
 20                  25                  30                  35 cat gtg tgt ggt ggc tct ctc gtg tct gag cag tgg gtg ctg tca gct        477
His Val Cys Gly Gly Ser Leu Val Ser Glu Gln Trp Val Leu Ser Ala
                 40                  45                  50 gct cac tgc ttc ccc agc gag cac cac aag gaa gcc tat gag gtc aag        525
Ala His Cys Phe Pro Ser Glu His His Lys Glu Ala Tyr Glu Val Lys
                 55                  60                  65 ctg ggg gcc cac cag cta gac tcc tac tcc gag gac gcc aag gtc agc        573
Leu Gly Ala His Gln Leu Asp Ser Tyr Ser Glu Asp Ala Lys Val Ser
             70                  75                  80 acc ctg aag gac atc atc ccc cac ccc agc tac ctc cag gag ggc tcc        621
Thr Leu Lys Asp Ile Ile Pro His Pro Ser Tyr Leu Gln Glu Gly Ser
     85                  90                  95 cag ggc gac att gca ctc ctc caa ctc agc aga ccc atc acc ttc tcc        669
Gln Gly Asp Ile Ala Leu Leu Gln Leu Ser Arg Pro Ile Thr Phe Ser
100                 105                 110                 115 cgc tac atc cgg ccc atc tgc ctc cct gca gcc aac gcc tcc ttc ccc        717
Arg Tyr Ile Arg Pro Ile Cys Leu Pro Ala Ala Asn Ala Ser Phe Pro
                120                 125                 130 aac ggc ctc cac tgc act gtc act ggc tgg ggt cat gtg gcc ccc tca        765
Asn Gly Leu His Cys Thr Val Thr Gly Trp Gly His Val Ala Pro Ser
                135                 140                 145 gtg agc ctc ctg acg ccc aag cca ctg cag caa ctc gag gtg cct ctg        813
Val Ser Leu Leu Thr Pro Lys Pro Leu Gln Gln Leu Glu Val Pro Leu
        150                 155                 160 atc agt cgt gag acg tgt aac tgc ctg tac aac atc gac gcc aag cct        861
Ile Ser Arg Glu Thr Cys Asn Cys Leu Tyr Asn Ile Asp Ala Lys Pro
    165                 170                 175 gag gag ccg cac ttt gtc caa gag gac atg gtg tgt gct ggc tat gtg        909
Glu Glu Pro His Phe Val Gln Glu Asp Met Val Cys Ala Gly Tyr Val
180                 185                 190                 195 gag ggg ggc aag gac gcc tgc cag ggt gac tct ggg ggc cca ctc tcc        957
Glu Gly Gly Lys Asp Ala Cys Gln Gly Asp Ser Gly Gly Pro Leu Ser
                200                 205                 210 tgc cct gtg gag ggt ctc tgg tac ctg acg ggc att gtg agc tgg gga       1005
Cys Pro Val Glu Gly Leu Trp Tyr Leu Thr Gly Ile Val Ser Trp Gly
                215                 220                 225 gat gcc tgt ggg gcc cgc aac agg cct ggt gta tac act ctg gcc tcc       1053
Asp Ala Cys Gly Ala Arg Asn Arg Pro Gly Val Tyr Thr Leu Ala Ser
            230                 235                 240 agc tat gcc tcc tgg atc caa agc aag gtg aca gaa ctc cag cct cgt       1101
Ser Tyr Ala Ser Trp Ile Gln Ser Lys Val Thr Glu Leu Gln Pro Arg
            245                 250                 255
```

```
gtg gtg ccc caa acc cag gag tcc cag ccc gac agc aac ctc tgt ggc    1149
Val Val Pro Gln Thr Gln Glu Ser Gln Pro Asp Ser Asn Leu Cys Gly
260             265                 270                 275 agc cac ctg gcc ttc agc tct gcc cca gcc cag ggc ttg ctg agg ccc    1197
Ser His Leu Ala Phe Ser Ser Ala Pro Ala Gln Gly Leu Leu Arg Pro
                280                 285                 290 atc ctt ttc ctg cct ctg ggc ctg gct ctg ggc ctc ctc tcc cca tgg    1245
Ile Leu Phe Leu Pro Leu Gly Leu Ala Leu Gly Leu Leu Ser Pro Trp
            295                 300                 305 ctc agc gag cac tgagctggcc ctacttccag gatggatgca tcacactcaa        1297
Leu Ser Glu His
            310 ggacaggagc ctggtccttc cctgatggcc tttggaccca gggcctgact tgagccactc  1357 cttccttcag gactctgcgg gaggctgggg ccccatcttg atctttgagc ccattcttct  1417 gggtgtgctt tttgggacca tcactgagag tcaggagttt tactgcctgt agcaatggcc  1477 agagcctctg gccccctcacc caccatggac cagcccattg ccgagctcc tggggagctc   1537 ctgggaccct tggctatgaa aatgagccct ggctcccacc tgtttctgga agactgctcc  1597 cggcccgcct gcccagactg atgagcacat ctctctgccc tctccctgtg ttctgggctg  1657 gggccacctt tgtgcagctt cgaggacagg aaaggcccca atcttgccca ctggccgctg  1717 agcgcccccg agccctgact cctggactcc ggaggactga gccccaccg gaactgggct   1777 ggcgcttgga tctggggtgg gagtaacagg gcagaaatga ttaaaatgtt tgagcac     1834
```

```
<210> SEQ ID NO 3
<211> LENGTH: 343
<212> TYPE: PRT
<213> ORGANISM: Homo sapiens

<400> SEQUENCE: 3

Met Ala Gln Lys Gly Val Leu Gly Pro Gly Gln Leu Gly Ala Val
        -30                 -25                 -20

Ile Leu Leu Tyr Leu Gly Leu Leu Arg Ser Gly Thr Gly Ala Glu Gly
        -15                 -10                 -5              -1

Ala Glu Ala Pro Cys Gly Val Ala Pro Gln Ala Arg Ile Thr Gly Gly
1               5                   10                  15

Ser Ser Ala Val Ala Gly Gln Trp Pro Trp Gln Val Ser Ile Thr Tyr
                20                  25                  30

Glu Gly Val His Val Cys Gly Gly Ser Leu Val Ser Glu Gln Trp Val
                35                  40                  45

Leu Ser Ala Ala His Cys Phe Pro Ser Glu His His Lys Glu Ala Tyr
            50                  55                  60

Glu Val Lys Leu Gly Ala His Gln Leu Asp Ser Tyr Ser Glu Asp Ala
65                  70                  75                  80

Lys Val Ser Thr Leu Lys Asp Ile Ile Pro His Pro Ser Tyr Leu Gln
                85                  90                  95

Glu Gly Ser Gln Gly Asp Ile Ala Leu Leu Gln Leu Ser Arg Pro Ile
                100                 105                 110

Thr Phe Ser Arg Tyr Ile Arg Pro Ile Cys Leu Pro Ala Ala Asn Ala
            115                 120                 125

Ser Phe Pro Asn Gly Leu His Cys Thr Val Thr Gly Trp Gly His Val
            130                 135                 140

Ala Pro Ser Val Ser Leu Leu Thr Pro Lys Pro Leu Gln Gln Leu Glu
145                 150                 155                 160
```

Val Pro Leu Ile Ser Arg Glu Thr Cys Asn Cys Leu Tyr Asn Ile Asp
            165                 170                 175

Ala Lys Pro Glu Glu Pro His Phe Val Gln Glu Asp Met Val Cys Ala
        180                 185                 190

Gly Tyr Val Glu Gly Gly Lys Asp Ala Cys Gln Gly Asp Ser Gly Gly
        195                 200                 205

Pro Leu Ser Cys Pro Val Glu Gly Leu Trp Tyr Leu Thr Gly Ile Val
    210                 215                 220

Ser Trp Gly Asp Ala Cys Gly Ala Arg Asn Arg Pro Gly Val Tyr Thr
225                 230                 235                 240

Leu Ala Ser Ser Tyr Ala Ser Trp Ile Gln Ser Lys Val Thr Glu Leu
                245                 250                 255

Gln Pro Arg Val Val Pro Gln Thr Gln Glu Ser Gln Pro Asp Ser Asn
            260                 265                 270

Leu Cys Gly Ser His Leu Ala Phe Ser Ser Ala Pro Ala Gln Gly Leu
        275                 280                 285

Leu Arg Pro Ile Leu Phe Leu Pro Leu Gly Leu Ala Leu Gly Leu Leu
    290                 295                 300

Ser Pro Trp Leu Ser Glu His
305                 310

<210> SEQ ID NO 4
<211> LENGTH: 19
<212> TYPE: PRT
<213> ORGANISM: Artificial
<220> FEATURE:
<223> OTHER INFORMATION: synthetic peptide

<400> SEQUENCE: 4

Pro His Pro Ser Tyr Leu Gln Glu Gly Ser Gln Gly Asp Ile Ala Leu
1               5                   10                  15

Leu Gln Leu

<210> SEQ ID NO 5
<211> LENGTH: 19
<212> TYPE: PRT
<213> ORGANISM: Artificial
<220> FEATURE:
<223> OTHER INFORMATION: synthetic peptide

<400> SEQUENCE: 5

Asn Cys Leu Tyr Asn Ile Asp Ala Lys Pro Glu Glu Pro His Phe Val
1               5                   10                  15

Gln Glu Asp

<210> SEQ ID NO 6
<211> LENGTH: 19
<212> TYPE: PRT
<213> ORGANISM: Artificial
<220> FEATURE:
<223> OTHER INFORMATION: synthetic peptide

<400> SEQUENCE: 6

Ala Gly Tyr Val Glu Gly Gly Lys Asp Ala Cys Gln Gly Asp Ser Gly
1               5                   10                  15

Gly Pro Leu

```
<210> SEQ ID NO 7
<211> LENGTH: 11
<212> TYPE: PRT
<213> ORGANISM: Artificial
<220> FEATURE:
<223> OTHER INFORMATION: synthetic peptide

<400> SEQUENCE: 7

Pro Gln Thr Gln Glu Ser Gln Pro Asp Ser Asn
1               5                   10

<210> SEQ ID NO 8
<211> LENGTH: 12
<212> TYPE: PRT
<213> ORGANISM: Artificial
<220> FEATURE:
<223> OTHER INFORMATION: synthetic peptide

<400> SEQUENCE: 8

Ala His Gln Leu Asp Ser Tyr Ser Glu Asp Ala Lys
1               5                   10

<210> SEQ ID NO 9
<211> LENGTH: 12
<212> TYPE: PRT
<213> ORGANISM: Artificial
<220> FEATURE:
<223> OTHER INFORMATION: synthetic peptide

<400> SEQUENCE: 9

Asp Ser Tyr Ser Glu Asp Ala Lys Val Ser Thr Leu
1               5                   10

<210> SEQ ID NO 10
<211> LENGTH: 12
<212> TYPE: PRT
<213> ORGANISM: Artificial
<220> FEATURE:
<223> OTHER INFORMATION: synthetic peptide

<400> SEQUENCE: 10

Ser Glu Asp Ala Lys Val Ser Thr Leu Lys Asp Ile
1               5                   10
```

US 9,017,957 B2

PROSTASIN PARTIAL PEPTIDE AND ANTI-PROSTASIN ANTIBODY

TECHNICAL FIELD

The present invention relates to a peptide consisting of a specific amino acid sequence of prostasin and an antibody against the peptide. Moreover, the present invention relates to a reagent for immunological assay containing the antibody and an immunological assay method using the antibody. Furthermore, the present invention relates to a diagnostic kit for prostasin-associated disease.

BACKGROUND ART

Prostasin is a serine protease which has been isolated from human seminal fluid. Prostasin localization in body fluids (seminal fluid and urine) of tissues has been reported, as revealed by radioimmunoassay (RIA) using an antiserum which was obtained with the use of purified prostasin as an antigen (Yu, J. X. et al., J. Biol. Chem., Vol. 269, pp. 18843-18848, 1994). Furthermore, full-length cDNA encoding human prostasin, the amino acid sequence thereof, and the structure thereof have already been reported (Yu, J. X. et al., J. Biol. Chem., Vol. 270, pp. 13483-13489, 1995).

Prostasin is present in the nature in the form of a complex formed by binding to an inhibitor protein or in a free form as in the case of other serine proteases. As prostasin inhibitor proteins, a prostasin-binding protein (PBP; PN-1) or hepatocyte growth factor activator inhibitor-1B (HAI-1) has been reported (Chen, L-M. et al., The Prostate, Vol. 59, pp. 1-12, 2004; and Fan B. et al., J. Biol. Chem., Vol. 280, pp. 34513-34520, 2005). A complex of prostasin with PBP has a molecular weight of approximately 82 kDa and is thermostable in the presence of SDS and a reducing agent. However, the presence of other inhibitors is predicted, in addition to the inhibitor proteins reported above. It is unknown that to what kinds of inhibitor proteins prostasin binds to form complexes in body fluids such as urine, seminal fluid, and blood.

The clinical significances of the measurement of prostasin, which have been reported, are: 1) the possible use thereof for diagnosis of hypertension; and 2) the possible use thereof as a tumor marker for diagnosis, for example. Diagnosis of hypertension with the use of the measurement of prostasin has been suggested, since prostasin has effects on the activation of the epithelial Na channel (ENaC) which is important for regulation of renal tubular Na reabsorption and body fluid volume (Narikiyo, T. et al., J. Clin. Invest., Vol. 109, pp. 401-408, 2002; and Olivieri, O. et al., Hypertension, Vol. 46, pp. 683-688, 2005). Moreover, the use of prostasin as a tumor marker has been suggested, since serum prostasin levels in epithelial ovarian cancer patients are found to be significantly higher than those in normal groups (Mok, S. C. et al., J. Natl. Cancer Inst., Vol. 93, pp. 1458-1464, 2001). For measurement of prostasin, immunoassays (e.g., radioimmunoassay, immunoblotting, ELISA, and Western blotting) have been performed using an antiserum or a monoclonal antibody. which are obtained by immunization with the use of purified natural prostasin as an antigen (for example, Yu, J. X. et al., 1994; Narikiyo, T. et al., 2002; Mok, S. C. et al., 2001; and Chen, L-M. et al., Prostate, Vol. 59, pp. 1-12, 2004). In addition a peptide is designed based on the amino acid sequence of a known prostasin, an antiserum or a monoclonal antibody is prepared using the peptide as an antigen for immunization, and the antiserum or the monoclonal antibody is used in immunoassays (e.g., Western blotting) (for example, Olivieri, O. et al., 2005).

However, natural prostasin can not be stably obtained. So, it has been difficult to obtain an antibody using natural prostasin as an antigen. In addition, prostasin has 6 disulfide bonds, making it difficult to obtain a protein having a correct conformation when recombinantly expressed. Therefore, an antibody generated against the recombinant prostasin does not always react with natural prostasin. Furthermore, although an antibody against a partial peptide of prostasin is known to react with prostasin under denaturation conditions (for example, in Western blotting) (for example, Production Information of Mouse Anti-Human Prostasin Antibody (Catalog No. 612173, produced by BD Biosciences), such antibody could not be used in immunoassays under non-denaturation conditions.

DISCLOSURE OF THE INVENTION

An object of the present invention is to provide an antibody that can be stably supplied and has high reactivity with prostasin under non-denaturation and denaturation conditions and an antigenic peptide for preparation of the antibody. Another object of the present invention is to provide an immunological assay method using the above antibody.

As a result of intensive studies to solve the objects, the present inventors have prepared an anti-prostasin antibody using a peptide comprising a specific amino acid sequence of human prostasin, and have found that the anti-prostasin antibody can specifically bind to prostasin under denaturation and non-denaturation conditions. Moreover, the present inventors have found that the above peptide can be used as a competitive substance in a competitive immunoassay using such anti-prostasin antibody. Based on these findings, the present inventors have completed the present invention.

The present invention encompasses the following (1) to (5).

(1) A peptide consisting of the amino acid sequence shown in SEQ ID NO: 1 or a peptide consisting of an amino acid sequence that has a deletion, a substitution, or an addition of one or several amino acids with respect to the amino acid sequence shown in SEQ ID NO: 1, and having antigenicity of prostasin.

The peptide can be used for preparation of an antibody against prostasin or purification of an antibody against prostasin. Also, a carrier protein may be bound to the peptide.

Furthermore, the peptide can be used as a competitive substance in a competitive immunoassay of prostasin. A label may be bound to the peptide.

(2) An antibody, which is prepared using the peptide according to (1) above as an antigen.

The antibody may be a polyclonal antibody or a monoclonal antibody. Furthermore, a label may be bound to the antibody. For example, a radioactive label, an enzyme label, or biotin may be bound thereto.

(3) A reagent for immunological assay for prostasin, containing the antibody according to (2) above.

The reagent for immunological assay may further contain the peptide according to (1) above.

(4) A method for detecting prostasin in a sample, comprising the following steps of:

(a) contacting the antibody according to (2) above with a sample; and (b) detecting whether or not the antibody binds to prostasin in a sample.

In step (a) of the above method, the peptide according to (1) above may also be added as a competitive substance.

Also, in the above method, the antibody is preferably bound to a solid phase. Furthermore, examples of a sample include, but are not limited to, urine, blood, serum, and plasma.

(5) A diagnostic kit for prostasin-associated disease, containing the antibody according to (2) above.

The diagnostic kit can be used for diagnosis of a prostasin-associated disease such as a disease selected from the group consisting of, but are not limited to, hypertension, ovarian cancer, prostate cancer, and breast cancer. Moreover, the diagnostic kit can also be used for more precise diagnosis of pathological conditions of hypertension due to hyperaldosteronemia such as primary aldosteronism.

This description includes part or all of the contents as disclosed in the description and/or drawings of Japanese Patent Application No. 2006-127575, which is a priority document of the present application.

BRIEF DESCRIPTION OF THE DRAWINGS

The patent or application filed contains at least one drawing executed in color. Copies of this patent or patent application publication with color drawing(s) will be provided by the Office upon request and payment of the necessary fee.

BEST MODE FOR CARRYING OUT THE INVENTION

Figure 1:
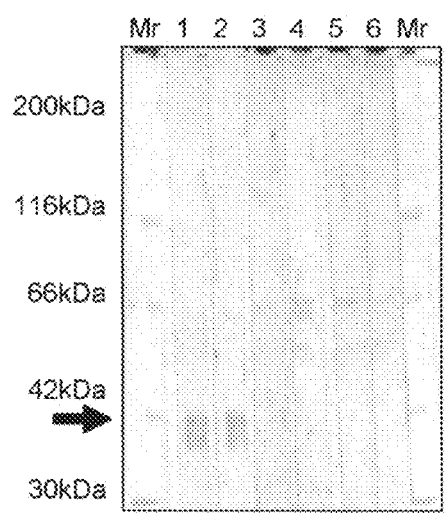
FIG. 1 shows the results of evaluating by a Western blotting method the reactivity of antisera (a) to (e) (obtained by immunization with partial peptides of prostasin) and the reactivity of a commercially available monoclonal antibody against prostasin-positive urine samples.
Figure 1:
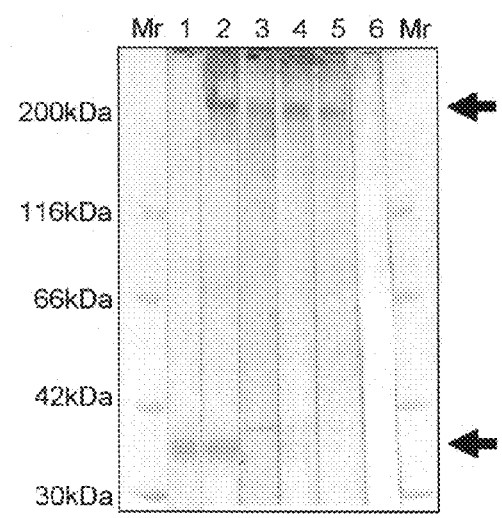

The present invention will be explained in detail as follows.
1. Partial Peptide of Human Prostasin Prostasin is a serine protease involved in regulation of vasoconstriction and regulation of body fluid volume. It is also known that the expression of prostasin decreases in prostate cancer but increases in ovarian cancer. Human prostasin has the amino acid sequence shown in SEQ ID NO: 3, which is encoded by the nucleotide sequence shown in SEQ ID NO: 2 (GenBank accession No. L41351). Human prostasin comprises a light chain (amino acids 1 to 12 in SEQ ID NO: 3) and a heavy chain (amino acids 13 to 252 in SEQ ID NO: 3). When the light chain is cleaved from the heavy chain (between amino acids 12 and 13 in SEQ ID NO: 3), an amino acid sequence comprising ITGG existing in the heavy chain is exposed so that it becomes an active serine protease.

The present invention relates to a partial peptide of the human prostasin, specifically a peptide consisting of 19 amino acids (SEQ ID NO: 1) which corresponds to amino acids 70 to 88 of the human prostasin shown in SEQ ID NO: 3. The peptide according to the present invention is herein referred to as a "partial peptide of human prostasin," or simply referred to as a "partial peptide." When an antibody is prepared using such partial peptide as an antigen, the thus obtained antibody can react not only with the partial peptide, but also with full-length human prostasin.

According to the present invention, the partial peptide may be a peptide consisting of an amino acid sequence that has a deletion, a substitution, or an addition of one or several amino acids with respect to the amino acid sequence shown in SEQ ID NO: 1, as long as the peptide has antigenicity of prostasin. For example, 1 to 5 amino acids, or preferably 1 to 3 amino acids may be deleted from the amino acid sequence shown in SEQ ID NO: 1, 1 to 5 amino acids, or preferably 1 to 3 amino acids may be added to the amino acid sequence shown in SEQ ID NO: 1, or 1 to 5 amino acids, and preferably 1 to 3 amino acids in the amino acid sequence shown in SEQ ID NO: 1 may be substituted with (an)other amino acids. The thus prepared amino acid sequences can be used in the present invention. In particular, conservative substitution of 1 or several amino acids in the amino acid sequence shown in SEQ ID NO: 1 is preferable. The term "conservative substitution" is known in the art and refers to that an amino acid is substituted with an amino acid having properties equivalent to those of the amino acid. For example, a neutral (polar) amino acid (Asn, Ser, Gln, Thr, Tyr, or Cys), a neutral (non-polar; that is, hydrophobic) amino acid (Gly, Trp, Met, Pro, Phe, Ala, Val, Leu, or Ile), an acidic (polar) amino acid (Asp or Glu), a basic (polar) amino acid (Arg, His, or Lys) is substituted with an amino acid having the equivalent properties.

Furthermore, for example, a peptide consisting of an amino acid sequence having at least 80% or more, preferably 90% or more, and particularly preferably 95% or more sequence homology or identity with the amino acid sequence shown in SEQ ID NO: 1 can also be used in the present invention. In addition, the homology or identity of an amino acid sequence can be easily determined by a method known in the art.

The term "antigenicity of prostasin" refers to the capability of an antigen, with which an anti-prostasin antibody can be prepared, and the capability of an antigen to react with an anti-prostasin antibody. Whether or not a peptide has antigenicity of prostasin can be confirmed by preparing an antibody against the peptide and then detecting whether or not the thus prepared antibody reacts with full-length (wild-type) prostasin, or detecting whether or not a peptide reacts with an anti-prostasin antibody.

The partial peptide of human prostasin may be chemically synthesized based on the amino acid sequence shown in SEQ ID NO: 1 or generated by transformation of a host using a nucleic acid encoding the partial peptide followed by collection of the peptide expressed in the host.

In the case of chemical synthesis, according to a known peptide synthesis technique, for example, the partial peptide of human prostasin can be synthesized using a commercially available peptide synthesizer or a commercially available peptide synthesis kit. Peptide synthesis techniques are described in literatures such as Peptide Synthesis, Interscience, New York, 1996; The Proteins, Vol. 2, Academic Press Inc., New York, 1976; Peptide Synthesis, MARUZEN Co., Ltd., 1975; and Basics and Experiments for Peptide Synthesis, MARUZEN Co., Ltd., 1985 or patent documents such as International Publication WO99/67288 (pamphlet), for example.

A peptide synthesis method may be either a solid phase method or a liquid phase method, as long as a target partial peptide sequence can be obtained. A solid-phase synthesis method is preferable in view of rapid synthesis of a compound (within a short time) on a solid-phase carrier (mainly a polystyrene resin: 100- to 500-mesh particles) and simple post treatment (because the carrier is insoluble in a solvent, and thus reagents after reaction can be removed only by washing with the solvent). For example, a partial peptide can be synthesized by a solid phase method based on an Fmoc (9-fluorenylmethoxycarbonyl)/PyBOP (benzoyl triazole-1-yl-oxy-tris-pyrrolidino-phosphonium-hexafluorophosphate) method. Specifically, synthesis can be performed by a stepwise extension method that involves repeating each step of deprotecting α amino group, washing, coupling, and washing with the use of a conventional Fmoc-wang resin, Fmoc-amino acid-wang resin, or the like as a starting resin and a protected amino acid corresponding to the sequence of a target partial peptide. Finally, the thus obtained peptide having a target sequence can be obtained by excising it from a resin binding thereto, washing, and then freeze-drying.

The partial peptide as an antigen for immunization can also be synthesized according to a MAP (Multiple Antigen Peptides) method (James P. Tam, Journal of Immunological Methods, vol. 196, 17-32 (1996)) so as to increase the antibody titer, in which synthesis is carried out using an Fmoc-MAP wang resin or the like instead of the above starting resin (e.g., an Fmoc-wang resin) in a manner similar to the above.

Moreover, when a gene recombination technique is employed, a nucleic acid encoding the partial peptide can be obtained by: extraction of RNA from a tissue or a cell of the prostate, bronchi, lungs, colon, salivary gland, pancreas, kidney, liver, or the like, or seminal fluid, and reverse transcription polymerase chain reaction (RT-PCR) using mRNA purified from the RNA and primers designed based on the human prostasin gene sequence; or screening of cDNA library using a probe designed based on the human prostasin gene sequence. Alternatively, a nucleic acid encoding the partial peptide can be obtained by extraction of DNA from a tissue or a cell of the prostate, bronchi, lungs, colon, salivary gland, pancreas, kidney, liver, or the like or seminal fluid, and nucleic acid amplification reaction (e.g., PCR) using the DNA as a template and primers designed based on the human prostasin gene sequence. Moreover, a method for preparation of a nucleic acid encoding the partial peptide with a mutation is known in the art.

In the present invention, an expression vector for recombinant expression of the partial peptide can be obtained by ligating the above nucleic acid to an appropriate vector. Furthermore, a transformant can be prepared by introducing the above nucleic acid or expression vector into host cells so that a peptide of interest can be expressed.

Any vector can be used and the vector includes a plasmid, a phagemid, or a virus-based vector or a known vector such as an artificial chromosome. Examples of plasmid DNA include plasmids derived from bacteria (e.g., pBluescript-based) and plasmids derived from yeast. Examples of phagemid DNA include λ phages (e.g., λgt10 and λZAP). Furthermore, transformants can be prepared using vectors based on animal viruses, such as retroviruses, adenoviruses, and vaccinia viruses, vectors based on insect viruses such as baculoviruses, bacterial artificial chromosomes (BACs), yeast artificial chromosomes (YACs), human artificial chromosomes (HACs), and the like.

For insertion of a nucleic acid into a vector, for example, a purified nucleic acid is cleaved with an appropriate restriction enzyme and inserted into a restriction enzyme site or a multicloning site of vector DNA, so as to ligate the insert to the vector. A vector should be constructed so that the vector is autonomously replicated in host cells or a nucleic acid on the vector is integrated into the genome of host cells and then the partial peptide of human prostasin is expressed in the host cells. Accordingly, in addition to a promoter and a nucleic acid, if desired a cis element such as an enhancer, a splicing signal, a polyA addition signal, a selection marker, a ribosome binding sequence (SD sequence), a homologous sequence, and the like are preferably ligated to a vector. In addition, examples of a selection marker include a dihydrofolate reductase gene, an ampicillin resistance gene, and a neomycin resistance gene. Furthermore, sequences such as a signal sequence, a His tag may also be added to facilitate the purification of the partial peptide. Known DNA ligase is used to ligate these various sequences to a vector. The above various sequences and a vector are annealed and then linked, so that an expression vector is constructed.

A host to be used for transformation is not particularly limited as long as it enables the expression of an introduced nucleic acid and is capable of producing the partial peptide of human prostasin. Examples of such a host include bacteria (e.g., *Escherichia coli*), yeast (e.g., *Saccharomyces cerevisiae*), animal cells (e.g., COS cells and CHO cells), and insects (e.g., silkworms, Sf9 cells, and Sf21 cells).

A method for introducing a nucleic acid or an expression vector into bacteria is not particularly limited, as long as such a method is used for introducing DNA into bacteria. Examples of such a method include a method using calcium ions and an electroporation. Furthermore, a method for introducing a nucleic acid or an expression vector into yeast is not particularly limited, as long as the method is used for introducing DNA into yeast. Examples of such a method include an electroporation, a method using spheroplast, and a method using lithium acetate. Furthermore, examples of a method for introducing a nucleic acid or an expression vector into animal cells, insects, or insect cells include an electroporation, a method using calcium phosphate, and a lipofection.

A transformant is selected using the properties of a marker gene that is contained within a gene to be introduced. For example, when a neomycin resistance gene is used, a cell showing resistance to a G418 drug is selected.

The partial peptide of human prostasin can be obtained by culturing the above transformant in which a nucleic acid encoding the partial peptide has been introduced and then collecting the partial peptide from the culture. The term "culture" refers to any of a culture supernatant, a cultured cell, and a cell lysate. A method for culturing a transformant in a medium is carried out according to a method generally employed for culturing hosts.

As a medium for culturing transformants obtained using bacteria or yeast as hosts, either a natural or a synthetic medium may be used which contains carbon sources, nitrogen sources, inorganic salts, and the like, and enables efficient culture of transformants. Culture is generally performed under aerobic conditions such as shaking culture or aerobic and stirred culture at approximately 20° C. to 40° C. for approximately 1 to 24 hours. During a culture period, pH is maintained around neutral pH. During culture, antibiotics such as ampicillin or tetracycline may be added to a medium, if necessary. Examples of a medium that is used for culturing a transformant obtained using animal cells as hosts include conventionally employed RPMI1640 and DMEM media and such media supplemented with a fetal calf serum and the like. Culture is generally carried out in the presence of 5% $CO_2$ at approximately 37° C. for approximately 1 to 7 days. During culture, if necessary an antibiotic such as kanamycin or penicillin may be added to a medium.

After culture, when the partial peptide is produced within cells or microorganisms, the protein (peptide) is extracted by disrupting the cells or microorganisms. In addition, when the partial peptide is produced outside the cells or microorganisms, the culture solution is used without any treatment or the cells or the microorganisms are removed by, for example, centrifugation.

The partial peptide chemically synthesized or generated by a gene recombination technique can be isolated and purified by one of or an adequate combination of biochemical methods generally employed for protein isolation and purification, such as ammonium sulfate precipitation, gel chromatography, ion exchange chromatography, and affinity chromatography.

Whether or not the partial peptide of interest is obtained can be confirmed by polyacrylamide gel electrophoresis, sodium dodecyl sulfate-polyacrylamide gel electrophoresis (SDS-PAGE), or the like.

The peptide according to the present invention can be used for preparing an antibody against prostasin. In this case, the peptide may be conjugated (bound) to a carrier protein to enhance the antigenicity. For example, the peptide can be conjugated to a carrier protein such as keyhole limpet hemocyanin (KLH), bovine serum albumin (BSA), or ovalbumin (OVA). These carrier proteins are known in the art and a commercially available kit is also marketed. Therefore, with the use of such a known method or kit, one or more of carrier proteins can be conjugated to the peptide according to the present invention. Moreover, the peptide according to the present invention can also be used for purification of an antibody against prostasin. In this case, the peptide according to the present invention is preferably immobilized on a solid phase such as beads or membranes.

Furthermore, the peptide according to the present invention can be used as a competitive substance in a competitive immunoassay for prostasin. For example, in a competitive immunoassay based on an anti-prostasin antibody and prostasin, as described below, the addition of the partial peptide as a competitive substance makes it possible to measure the amount of prostasin that has reacted with an anti-prostasin antibody. A label or labels may be bound to the partial peptide of prostasin in order to facilitate detection. For example, biotin, a radioactive label, an enzyme label, or a fluorescent label can be bounded. The partial peptide of prostasin is preferably labeled with a radioisotope, a fluorescent substance, or biotin in view of avoidance of steric hindrance resulting from increases in the molecular weight of a label molecule during antigen-antibody reactions. In particular, the partial peptide is preferably labeled with biotin in view of reproducibility.

2. Antibody Against Partial Peptide

The present invention relates to an anti-prostasin antibody that is prepared using the above partial peptide of prostasin as an antigen. The thus obtained anti-prostasin antibody can specifically react not only with the partial peptide used as an antigen, but also with full-length prostasin.

(1) Preparation of Immunogen

An immunogen is prepared by dissolving the partial peptide of human prostasin or such partial peptide conjugate with a carrier protein obtained as described above as an antigen in a buffer. In addition, if necessary, an adjuvant may also be added to carry out immunization effectively. Examples of such an adjuvant include commercially available complete Freund's adjuvant (FCA) and incomplete Freund's adjuvant (FIA). These adjuvants can be used independently or used after mixing them.

(2) Preparation of Polyclonal Antibody

When a polyclonal antibody is prepared, an immunogen is administered to an animal such as a mammal or a bird (e.g., a rabbit, a rat, a mouse, a goat, a chicken, or a duck). Immunization is mainly performed by intravenous injection, subcutaneous injection, intraperitoneal injection, or injection into a footpad. Furthermore, immunization intervals are not particularly limited, and immunization is carried out once to 5 times at intervals of several days to several weeks. Subsequently, on days 20 to 90 after final immunization, serum or egg yolk is collected, the antibody titer is measured by an immunoassay such as an enzyme-linked immunosorbent assay (ELISA), an enzyme immunoassay (EIA), or a radioimmunoassay (RIA). The antibodies are collected on the day at which the maximum antibody titer is observed. Thereafter, the reactivity of a polyclonal antibody specific to the partial peptide of prostasin in the serum or the egg yolk is measured by the above immunoassay or the like.

An antiserum can also be directly used for an immunological assay method. However, it is preferable to purify and then use an antibody or antibodies in an antiserum by performing affinity chromatography, protein A or protein G affinity chromatography, or the like using a partial peptide of prostasin.

(3) Preparation of Monoclonal Antibody

When a monoclonal antibody is prepared, an immunogen is administered to a mammal such as a rabbit, a rat, or a mouse. Immunization is mainly performed by intravenous injection, subcutaneous injection, intraperitoneal injection, or injection into a footpad. Furthermore, immunization intervals are not particularly limited, and immunization is carried out once to 5 times at intervals of several days to several weeks. Subsequently, on days 20 to 90 after final immunization, antibody-producing cells are collected. Examples of antibody-producing cells include spleen cells, lymph node cells, and peripheral blood cells.

To establish hybridomas, antibody-producing cells can be fused with myeloma cells. As myeloma cells to be fused to antibody-producing cells, cells of generally available established cell lines can be used. Cell lines that are preferably used herein have drug selectivity and properties such that they cannot survive in an HAT selection medium (containing hypoxanthine, aminopterin, and thymidine) in an unfused state, but can survive only in a state of being fused to antibody-producing cells. Examples of myeloma cells include cells of mouse myeloma cell lines such as P3X63-Ag.8.U1 (P3U1) and NS-I.

Next, the above myeloma cells are fused to antibody-producing cells. Cell fusion is carried out by mixing antibody-producing cells with myeloma cells in a medium for culturing animal cells, such as a serum-free DMEM or RPMI-1640 medium, and then carrying out fusion reaction in the presence of a cell fusion promoter (e.g., polyethylene glycol). Moreover, cell fusion can also be carried out using a commercially available cell fusion apparatus using electroporation.

Hybridomas of interest can be selected from cells after cell fusion treatment. For example, a cell suspension is adequately diluted with an RPMI-1640 medium or the like containing fetal calf serum and then seeded on a microtiter plate. A selection medium is added to each well and then cells are cultured while exchanging selection media appropriately. As a result, cells that grow on roughly day 30 after the initiation of culture using selection media can be obtained as hybridomas.

Next, culture supernatants of hybridomas that have grown are screened for the presence of antibodies reacting with a partial peptide of human prostasin. Screening of hybridomas can be performed according to a conventional method. For example, an enzyme-linked immunosorbent assay (ELISA), an enzyme immunoassay (EIA), a radioimmunoassay (RIA), or the like can be employed. Cloning of fused cells can be carried out by a limiting dilution or the like, so that a hybridoma producing a monoclonal antibody of interest is established.

As a method for collecting a monoclonal antibody from the thus established hybridoma, a general cell culture method, an ascite-formation method, or the like can be employed. When such method for collecting an antibody requires purification of the antibody, purification can be carried out by adequately selecting or adequately combining known methods such as an ammonium sulfate precipitation method, ion exchange chromatography, gel filtration, and affinity chromatography.

Globulin types of monoclonal antibodies, which can be used in the present invention, are not particularly limited, as long as they have activity of binding specifically to human prostasin. Globulin types may be any of IgG, IgM, IgA, IgE, and IgD and are preferably IgG and IgM.

(4) Other Antibodies

Furthermore, a nucleic acid based on the antibody molecule (prepared as described above) having antigen specificity to human prostasin is spliced together with a nucleic acid based on a human antibody molecule having appropriate biological activity to generate a chimeric antibody (Morrison et al., 1984, Proc. Natl. Acad. Sci., 81: 6851-6855; Neuberger et al., 1984, Nature, 312: 604-608; Takeda et al., 1985, Nature, 314: 452-454) can be prepared. Moreover, a single-chain antibody (U.S. Pat. No. 4,946,778; Bird, 1988, Science 242: 423-426; Huston et al., 1988, Proc. Natl. Acad. Sci. U.S.A. 85: 5879-5883; Ward et al., 1989, Nature 334: 544-546), a $F(ab')_2$ fragment, a Fab fragment, and the like can also be prepared using techniques known in the art.

An antibody that is prepared using the peptide according to the present invention as an antigen can specifically bind to natural (wild-type) human prostasin under denaturation conditions and non-denaturation conditions.

3. Reagent for Immunological Assay and Immunoassay for Prostasin

Prostasin can be detected in a sample using an antibody prepared as described above. The detection can be carried out based on any method, as long as it is a measurement method using antibodies; that is, an immunological assay. For example, prostasin can be detected using an immunohistochemical staining and an immunoelectron microscopy, and an immunoassay (e.g., an enzyme immunoassay (ELISA or EIA), a fluorescence immunoassay, a radioimmunoassay (RIA), an immunochromatography, and a Western blotting), for example.

Examples of test samples include, but are not particularly limited to, tissue or cell samples (such as prostate, bronchi, lungs, colon, salivary gland, pancreas, kidney, liver, cancer tissues, or cells), biological fluid samples (e.g., blood, serum, plasma, urine, spinal fluid, saliva, sweat, and ascites). For example, urine, blood, serum, plasma, or the like is preferably used as a sample. Particularly, urine or blood is more preferable in view of easiness for collection. Furthermore, a urine sample is further more preferable in view of liability relief for patients.

In the immunological assay of the present invention, prostasin is detected by causing prostasin in a sample to bind to the antibody according to the present invention and then detecting the bonds. The term "detection" in the present invention refers to simple detection of the presence or the absence of prostasin and also quantitative detection of prostasin.

Immunoassay for prostasin typically comprises contacting a test target sample with the antibody according to the present invention and then detecting the antibody binding to prostasin using a technique known in the art. By contact (contacting), it means that a condition is realized by which prostasin existing in a sample can come close to the antibody according to the present invention to bind to each other. For example, contacting includes procedures such as mixing of a liquid sample with an antibody-containing solution, coating a solid sample with an antibody-containing solution, and immersing a solid sample in an antibody-containing solution.

Immunoassay may be carried out using either a liquid phase system or a solid phase system. In view of the easiness of detection, the use of a solid phase system is preferred. Moreover, the format of an immunoassay is also not limited and may be, in addition to a direct solid phase method, a sandwich method, a competitive method, or the like.

The anti-prostasin antibody according to the present invention can specifically bind to and detect prostasin under either denaturation conditions (reducing conditions) or non-denaturation conditions. The anti-prostasin antibody according to the present invention can bind to prostasin in any form (for example, a form of a complex with an inhibitor protein and a free form). Therefore, the anti-prostasin antibody according to the present invention can be used in various formats of immunoassay, in addition to Western blotting using denaturation conditions.

Assay procedures can be performed by known methods (Ausubel, F. M. et al. (eds), Short Protocols in Molecular Biology, Chapter 11 "immunology" John Wiley & Sons, Inc. 1995). For example, Western blotting can be used. Alternatively, a complex of prostasin and an antibody can be separated by a known separation means (e.g., a chromatography method, a salting-out, an alcohol precipitation, an enzyme method, and a solid phase method) and then the signal of the label can be detected.

As an example of an immunoassay, when a solid-phase system is used, for example, antibodies may be immobilized onto a solid-phase support or carrier (e.g., a resin plate, a membrane, or a bead) or a sample may also be immobilized thereon. For example, antibodies are immobilized onto a solid-phase support, the support is washed with an appropriate buffer, and then the support is treated using the anti-prostasin antibody of the present invention. Next, the solid-phase support is subjected to second washing using a buffer, so as to remove unbound antibodies. The amount of bound antibodies on the solid support is detected by conventional means, and the binding of prostasin in a sample with the antibodies can be detected.

The binding activity of an antibody can be measured according to a known method. A measurement method effective and optimum for each assay can be determined by a person skilled in the art depending on the type and the format of immunoassay to be employed, the type and the subject of a label to be used, and the like.

In an embodiment of the present invention, to easily detect reaction of the anti-prostasin antibody of the present invention with prostasin existing in a sample, such reaction is directly detected by labeling the antibody of the present invention or such reaction is indirectly detected using a labeled secondary antibody, a biotin-avidin complex, or the like. Examples of labels and methods for detecting such labels, which can be used in the present invention, are as described below.

In the case of an enzyme immunoassay, peroxidase, β-galactosidase, alkaline phosphatase, glucoseoxidase, acetylcholinesterase, lactate dehydrogenase, and amylase can be used, for example. Furthermore, an enzyme inhibitor, a coenzyme, or the like can also be used. These enzymes can be bound to antibodies by a known method using a cross-linking agent such as glutaraldehyde or a maleimide compound.

In the case of a fluorescence immunoassay, fluorescein isothiocyanate (FITC), tetramethylrhodamineisothiocyanate (TRITC), and the like can be used. These fluorescent labels can be bound to antibodies by conventional techniques.

In the case of a radioimmunoassay, tritium, iodine$^{125}$, iodine$^{131}$, and the like can be used. Radioactive labels can be bound to antibodies by a known method such as a chloramine T method or Bolton-Hunter method.

For example, when the antibody of the present invention is directly labeled with a label or labels as described above, a sample is caused to come into contact with the labeled antibody of the present invention to form a prostasin-antibody complex. Unbound labeled antibodies are then separated and then the amount of prostasin in the sample can be measured based on the amount of the bound labeled antibodies or the amount of unbound labeled antibodies.

Furthermore, for example, when a labeled secondary antibody is used, the antibody of the present invention is reacted with a sample (primary reaction), and then the labeled secondary antibody is reacted with the obtained complex (secondary reaction). The primary reaction and the secondary reaction may be performed in reverse order, simultaneously, or at different times. By the primary reaction and the secondary reaction, the complex of prostasin—the antibody of the present invention—a labeled secondary antibody, or the complex of the antibody of the present invention—prostasin—a prostasin-labeled secondary antibody is formed. Unbound labeled secondary antibodies are separated from and then the amount of prostasin in the sample can be measured based on the amount of the bound labeled secondary antibodies or the amount of unbound labeled secondary antibodies.

When a biotin-avidin complex system is used, biotinylated antibodies are reacted with a sample and then labeled avidin is reacted with the thus obtained complexes. Avidin can specifically bind to biotin. Hence, binding of antibodies with prostasin can be measured by detecting signals from the labels added to avidin. Labels to be added to avidin are not particularly limited. For example, an enzyme label (e.g., peroxidase or alkaline phosphatase) is preferable.

Signals from labels can be detected according to a method known in the art. For example, when enzyme labels are used, enzyme activity is determined by adding substrates that cause color development as a result of degradation via enzymatic action and optically measuring the amount of the substrates degraded. Then, the obtained enzyme activity is converted into an amount of bound antibodies such that the amount of antibodies is calculated based on comparison with a standard level. Substrates may vary depending on types of enzyme to be used. For example, when peroxidase is used as an enzyme, 3,3',5,5'-tetramethylbenzidine (TMB), diaminobenzidine (DAB), or the like can be used. When alkaline phosphatase is used as an enzyme, paranitrophenol or the like can be used. Fluorescent labels can be detected and quantified using a fluorescence microscope, a plate reader, or the like. When a radioactive label is used, the radiation dose emitted from a radioactive label is measured using a scintillation counter, or the like.

In the present invention, it is preferable to detect prostasin in a sample using a competitive immunoassay. In this case, competitive substances or antibodies are labeled. Competitive substances to be used herein are not particularly limited, as long as they can bind to the anti-prostasin antibody of the present invention. For example, the partial peptide as described in the previous section, "1. Partial peptide of human prostasin," can be used. Preferably, a partial peptide used for preparation of an antibody to be used in a competitive immunoassay is used. Furthermore, a biotin-labeled partial peptide of prostasin is preferable as a competitive substance.

In an embodiment of the competitive immunoassay, competitive substances are immobilized onto a solid phase, blocking is performed, and then labeled antibodies and a sample are added. After a given time of reaction, the solid phase is washed to remove unbound antibodies and the sample and then signals from the labels on the solid phase are detected. The amount of prostasin in the sample can be measured by measuring the degree of inhibition of binding between labeled antibodies and competitive substances due to addition of the sample. In another embodiment, after immobilization of antibodies onto a solid phase, a sample and labeled competitive substances are added to carry out reaction for a given period of time, unbound competitive substances and the sample are removed by washing, and then signals from the labels on the solid phase are detected. Thus, the amount of prostasin in the sample can be measured by measuring the degree of inhibition of binding between the labeled competitive substances and the antibodies due to the addition of the sample.

The antibody according to the present invention can also be used histologically for in situ detection of prostasin, as in the case of an immunohistochemical staining (for example, an immunostaining) or immunoelectron microscopy. In situ detection can be carried out by excising a histological sample from a subject (e.g., a paraffin-embedded tissue section) and then causing a labeled antibody to come into contact with the sample.

Furthermore, the present invention relates to a reagent for immunological assay for prostasin containing the anti-prostasin antibody of the present invention. In the reagent for immunological assay of the present invention, the anti-prostasin antibody may be labeled. Moreover, the anti-prostasin antibody may be immobilized on a solid-phase support (for example, membranes and beads).

The reagent for immunological assay may contain, in addition to the anti-prostasin antibody of the present invention, components useful for implementation of an immunological assay. Examples of such components include a competitive substance, a buffer, a reagent for treatment of a sample, and a label, which are used in immunoassays. A competitive substance contained in the reagent for immunological assay may be labeled and/or immobilized on a solid-phase support.

The above-described detection of prostasin can be easily and simply carried out using the reagent for immunological assay of the present invention.

4. Other Applications

Furthermore, the antibody of the present invention specifically reacts with prostasin as described above, so it can be used for a diagnostic kit for diseases associated with prostasin. The term "disease(s) associated with prostasin" refers to a disease(s) characterized in that the conditions of the disease correlate with the overexpression or the underexpression of prostasin. For example, hypertension, ovarian cancer, or the like can be diagnosed by detection of the overexpression of prostasin. Moreover, prostate cancer, breast cancer, or the like can be diagnosed by detection of the underexpression of prostasin.

Furthermore, in blood (for example, plasma) or urine, a prostasin level positively correlates with an aldosteron level. Here, aldosteron, which is a type of adrenal cortex hormone, is a mineral corticoid that exerts the action of strong electrolyte metabolism, by which sodium ions and water in body are maintained and excretion of potassium ions are promoted. Aldosteron promotes the expression of prostasin. Hence, it has been reported that the overexpression of prostasin may lead to the positive feedback of the production of aldosteron (Narikiyo, T. et al., 2002, supra; Olivieri, O. et al., 2005, supra; and Wang C et al., Am J Physiol Regul Integr Comp Physiol., Vol. 284, No. 4, pp. 1031-1036, 2003). Therefore, through detection of the overexpression of prostasin, the pathological conditions of hypertension due to hyperaldosteronemia such as primary aldosteronism can be diagnosed more precisely.

The diagnostic kit of the present invention comprises the above described anti-prostasin antibody of the present invention. Therefore, prostasin in a sample collected from a subject suspected of being affected with a disease is detected with the use of the diagnostic kit of the present invention, so that whether the subject is affected with the disease can be rapidly and simply determined. Such diagnostic kit for diseases using an immunological assay is known. Persons skilled in the art can easily select appropriate components other than antibodies. Moreover, the diagnostic kit of the present invention can also be used in any techniques, as long as they are techniques to carry out immunological assays.

The present invention will be described in detail by examples as follows, but the present invention is not limited by these examples.

Example 1

In this example, a partial peptide of human prostasin was synthesized.

First, a partial peptide (a) of prostasin having the amino acid sequence of SEQ ID NO: 1 indicated below was synthesized:

a):
(SEQ ID NO: 1)
Ala-His-Gln-Leu-Asp-Ser-Tyr-Ser-Glu-Asp-Ala-Lys-

Val-Ser-Thr-Leu-Lys-Asp-Ile

The partial peptide (a) was synthesized by the Fmoc (9-fluorenylmethoxycarbonyl)/PyBOP (benzoyl triazole-1-yl-oxy-tris-pyrrolidino-phosphonium-hexafluorophosphate) solid phase peptide method using an automated peptide synthesizer (PSSM-8, produced by Shimadzu Corporation).

Specifically, an Fmoc-Ile-wang resin was used as a starting resin after initial washing thereof (DMF 600 µL, 180 seconds, once). A stepwise extension method was carried out, by which the steps of deprotection of a amino group (30% piperidine/DMF (500 µL), 180 seconds, twice), washing (DMF (600 µL), 60 seconds, 5 times), coupling (each α amino group-protected amino acid (1 mmol), 30 minutes), and washing (DMF 600 µL, 60 seconds, 5 times) were repeated by sequentially using the protected amino acids, Fmoc-Asp (OtBu)-OH, Fmoc-Lys(Boc)-OH, Fmoc-Leu-OH, Fmoc-Thr (tBu)-OH, Fmoc-Ser(tBu)-OH, Fmoc-Val-OH, Fmoc-Lys (Boc)-OH, Fmoc-Ala-OH, Fmoc-Asp(OtBu)-OH, Fmoc-Glu(OtBu)-OH, Fmoc-Ser(tBu)-OH, Fmoc-Tyr(tBu)-OH, Fmoc-Ser(tBu)-OH, Fmoc-Asp(OtBu)-OH, Fmoc-Leu-OH, Fmoc-Gln(Trt)-OH, Fmoc-His(Trt)-OH, and Fmoc-Ala-OH. Finally, the thus obtained peptide was excised from the binding resin using 4.7 mL of trifluoroacetic acid, 0.25 mL of anisole, 0.05 mL of ethanedithiol, washed twice using anhydrous ether, and then freeze-dried.

The thus obtained peptides were each analyzed and fractionated using an HPLC system (produced by Waters, Waters 600E) and µBondasphere 5µ C18 100A column (150×3.9 mm for fractionation and 150×19 mm for analysis). Furthermore, amino acid analysis was carried out by the Pico-Tag method. Identity was confirmed by FAB mass spectroscopy. As a result, the partial peptide (a) with purity of 98.3% was obtained.

Subsequently, partial peptides (b) to (h) of prostasin were synthesized according to processes similar to those employed for (a) above:

b):
(SEQ ID NO: 4)
Pro-His-Pro-Ser-Tyr-Leu-Gln-Glu-Gly-Ser-Gln-Gly-

Asp-Ile-Ala-Leu-Leu-Gln-Leu c):
(SEQ ID NO: 5)
Asn-Cys-Leu-Tyr-Asn-Ile-Asp-Ala-Lys-Pro-Glu-Glu-

Pro-His-Phe-Val-Gln-Glu-Asp d):
(SEQ ID NO: 6)
Ala-Gly-Tyr-Val-Glu-Gly-Gly-Lys-Asp-Ala-Cys-Gln-

Gly-Asp-Ser-Gly-Gly-Pro-Leu e):
(SEQ ID NO: 7)
Pro-Gln-Thr-Gln-Glu-Ser-Gln-Pro-ASp-Ser-Asn f):
(SEQ ID NO: 8)
Ala-His-Gln-Leu-Asp-Ser-Tyr-Ser-Glu-Asp-AIa-Lys g):
(SEQ ID NO: 9)
Asp-Ser-Tyr-Ser-Glu-Asp-Ala-Lys-Val-Ser-Thr-Leu h):
(SEQ ID NO: 10)
Ser-Glu-Asp-Ala-Lys-Val-Ser-Thr-Leu-Lys-Asp-Ile.

As a result, all of the partial peptides (b) to (h) had purity of 95% or higher.

Example 2

In this example, anti-prostasin antibodies were prepared.
(1) Immunization of Rabbit Three rabbits were each immunized by a known method using the 5 types of partial peptide, (a) to (e), obtained in Example 1 above. Specifically, Freund's complete adjuvant (FCA) and a solution of each of the 5 types of partial peptide, (a) to (e), obtained in Example 1 above were stirred in a syringe to prepare emulsions. Each rabbit (Japanese white) was immunized four times in total by intradermal administration of 0.5 mg per animal of the emulsion every 2 weeks. However, from the second immunization, Freund's incomplete adjuvant was used instead of FCA.

Seventy days after primary immunization, small amounts of blood were collected from the immunized rabbits. Increases in antiserum titer were confirmed by the ELASA method using partial peptide-immobilized plates. Thereafter, large amounts of blood were collected from the rabbits. The collected blood was kept at room temperature for 3.5 hours and then transferred to a low-temperature room for 48 hours to cause clot formation. Subsequently, centrifugation was performed at 3,000 g, so that sera were obtained.

As a result, strong increases in antibody titer were observed when immunization with the 3 types of partial peptide, (a), (c), and (e), had been performed. The antisera obtained by immunization with the partial peptides (a) to (e) were determined to be antisera (a) to (e), respectively.

(2) Reactivity of Antibody

Trichloroacetic acid (final: 15%) was previously added to a prostasin urine sample and then the sample was allowed to stand for 1 hour. The protein was spun down at 12000 r.p.m., cold ethanol (−40° C.) was added to the sample, centrifugation was repeated at 12000 r.p.m. for 3 times. And then the sample was finally treated with an SDS sample treatment solutions containing or not containing a reducing agent.

To examine the reaction specificity of the rabbit antisera obtained in (1) above, the samples treated with the SDS sample treatment solution containing the reducing agent or the samples treated with the SDS sample treatment solution containing no reducing agent were subjected to SDS electrophoresis. The Western blotting was then carried out using the antisera. In addition, the amount of the solution applied to one lane was 10 μL or 1 mL in terms of original urine volume.

Specifically, samples were each subjected to an electrophoresis on 4% to 20% gradient acrylamide gel (produced by Daiichi Pure Chemicals Co., Ltd.) with constant current. Moreover, regarding samples for electrophoresis, one volume of a sample treatment solution (312.5 mM Tris-hydrochloric acid, pH 6.8, 0.1% BPB, 10% SDS, 25% 2-mercaptoethanol, and 20% glycerin) containing a 5-fold reducing agent (mercaptoethanol) or a sample treatment solution containing no reducing agent was previously added to four volumes of a test sample solution and then heat treatment was carried out at 95° C. for 3 minutes. A protein molecular weight marker II "Daiichi" (Daiichi Pure Chemicals) was used as a standard molecular weight marker.

After electrophoresis, the resultant was transferred onto a nitrocellulose membrane (BIO RAD, pore size 0.45 μm). After transfer, the nitrocellulose membrane was blocked with a 5% bovine serum albumin solution. After blocking, 5 types of rabbit antiserum, (a) to (e), diluted 50 folds with a Tris buffer containing 0.2% bovine serum albumin and a commercially available anti-prostasin mouse monoclonal antibody (BD Biosciences, catalog No. 612173) diluted 250 folds with the same were each added to react at room temperature for 1.5 hours. After reaction, washing was carried out. A POD-labeled anti-rabbit IgG antibody (Amersham Pharmacia, code No. NA9340) and a POD-labeled anti-mouse IgG antibody (Amersham Pharmacia, code No. NA9310V), which had been diluted 500 folds with a Tris buffer containing 0.2% bovine serum albumin, were added to react at room temperature for 1 hour. After reaction, the nitrocellulose membranes were washed. Color developing was carried out with a TMB Membrane Peroxidase Substrate System (3-C) (KPL).

The results are shown in FIG. 1. FIG. 1A shows the results obtained under reducing conditions. "Mr" denotes a molecular weight marker, lane 1 denotes the reaction using the commercially available mouse monoclonal antibody (250 folds dilutions), lanes 2 to 6 denote the results of the reaction of the rabbit antisera (a) to (e) (100 folds dilutions), respectively. FIG. 1B shows the results obtained under nonreducing conditions. "Mr" denotes a molecular weight marker, lane 1 denotes the commercially available monoclonal antibody (BD Biosciences, catalog No. 612173) (250 folds dilutions), and lanes 2 to 6 denote the results of the reaction of the rabbit antisera (a) to (e) (100 folds dilutions), respectively. For the rabbit antisera, a POD-labeled anti-rabbit antibody (500 folds dilutions) was used as a secondary antibody. For the commercially available mouse monoclonal antibody, a POD-labeled anti-mouse antibody (500 folds dilutions) was used.

As shown in FIG. 1, when the antiserum (a) obtained by immunization with the partial peptide (a) of SEQ ID NO: 1 was used, a single band of approximately 40 kDa was clearly observed under reducing conditions and two bands (a band of approximately 37 kDa and a band of 200 kDa or more) were clearly observed under non-reducing conditions. On the other hand, when the commercially available mouse monoclonal antibody was used, under reducing conditions, a single band of approximately 40 kDa was confirmed similarly to the case of the antiserum (a). However, under non-reducing conditions, only a band of approximately 37 kDa was confirmed, and no reactivity with respect to the bands of 200 kDa or more was observed. Based on these results, it was revealed that the antiserum (a) obtained by immunization with the partial peptide (a) prepared in Example 1 has strong reactivity to prostasin even in a higher-molecular-weight form under non-reducing conditions.

Example 3

In this example, antibodies were purified from the antisera prepared in Example 2.

According to general procedures, 6.0 mg of the partial peptide (a) of SEQ ID NO: 1 was bound to 4 mL of CNBr-activated Sepharose 4B (Amersham Pharmacia Biotec) to prepare an immunosorbent column. Five mL each of the rabbit antiserum (a) (rabbit No. 1, No. 2, or No. 3) was applied to the above column. After application, the column was washed with an equilibrated phosphate buffer (PBS; 0.15 M NaCl, pH 7.3) until the absorbance at 280 nm reached ≤0.01 (in 5 volumes of the column). Next, elution was carried out with a 0.1 M glycine-0.5 M NaCl elution buffer (pH 2.8) and then the eluate was dialysed against an equilibrated PBS buffer.

The yields of specific antibodies eluted from the antisera (5 mL each); that is, from rabbit No. 1, No. 2, and No. 3, were 2.93 mg (0.122 mg/mL×24 mL), 2.72 mg (0.124 mg/mL×22 mL), and 3.05 mg (0.117 mg/mL×26 mL), respectively.

Similarly to the case of the above partial peptide (a) and antiserum (a), purification was carried out for the partial peptides (c) and (e) obtained in Example 1 and the two types of antiserum, (c) and (e), obtained in Example 2. Purified antibodies obtained as described above from the antisera (a), (c), and (e) were determined to be affinity-purified antibodies (a), (c), and (e), respectively.

Example 4

In this example, competitive immunoassays were carried out using antibodies prepared in Examples 2 and 3.

(1) Preparation of Antibody-Immobilized Plate

Three types of affinity-purified antibody, (a), (c), and (e) (protein concentration: 10 μg/mL) prepared in Example 3 were each diluted with a phosphate buffer (PBS; 0.15 M NaCl, pH 7.3), and dispensed at 100 μL per well in a microtiter plate (Nunc, Maxisorp). The plate was placed under refrigeration for 16 hours for immobilization. Subsequently, 1% BSA diluted with PBS (pH 7.3) was dispensed at 300 μL per well and then the plate was allowed to stand at room temperature for 2 hours for blocking.

Then, a 20% blocking reagent N101 for immunological assay (produced by NOF CORPORATION: code: S410-03012) diluted with PBS (pH 7.3) was dispensed at 300 μL per well and then allowed to stand at room temperature for 2 hours for blocking.

(2) Preparation of Pod-Labeled Antigen and Confirmation of Optimum Antigen Concentration Partial peptides (a), (c), and (e), and a recombinant protein of full-length prostasin, which correspond to the affinity-purified antibodies (a), (c), and (e) obtained in Example 3, and a commercially available anti-prostasin mouse monoclonal antibody (BD Biosciences, catalog No. 612173), respectively, were labeled with peroxidase (POD). They were prepared as POD-labeled antigens.

Prior to the competitive immunoassay, with the use of plates onto which the affinity-purified antibodies (a), (c), and (e) obtained in Example 3 and the commercially available anti-prostasin mouse monoclonal antibody (BD Biosciences, catalog No. 612173) had been immobilized, predetermined levels (0, 50, 100, and 500 ng/mL) of the partial peptides (a), (c), and (e) and the recombinant protein of full-length prostasin (prepared according to the method of Chen, L-M. et al., J. Biol. Chem., Vol. 276, pp. 21434-21442, 2001, specifically described on page 21435)) were added as antigens to carry out the invention. Furthermore, the above-prepared POD-labeled partial peptides (a), (c), and (e), and the POD-labeled recombinant protein of full-length prostasin were added as competitive substances while varying the concentrations (0.025, 0.05, 0.10, 0.15, 0.20, and 0.25 μg/mL) in the reaction. The presence or the absence of competitive reaction and the optimum concentrations of the POD-labeled antigens (competitive substances) for use were examined.

As a result, competitive reaction was observed when the combination of the partial peptide (a) and the POD-labeled competitive substance thereof was used. No competitive reaction was observed in the combinations of other partial peptides (c) and (e) and the recombinant protein of full-length prostasin with the POD-labeled competitive substances thereof.

The results obtained when the affinity-purified antibody (a)-immobilized plate was used and the varying concentration (0.025, 0.05, 0.1, 0.15, 0.20, and 0.25 μg/mL) of the POD-labeled partial peptide (a) was added in the presence of the predetermined levels of the unlabeled partial peptide (a) (0 and 50 ng/mL) are shown in the following Table 1 and FIG. 2.

TABLE 1

| | POD-labeled peptide concentration [μg/mL] | | | | | |
|---|---|---|---|---|---|---|
| | 0.025 | 0.05 | 0.10 | 0.15 | 0.20 | 0.25 |
| Unlabeled partial peptide (a) 0 ng/mL [absorbance (Abs)] | 0.418 | 0.815 | 1.405 | 2.044 | 2.399 | 2.913 |
| Unlabeled partial peptide (a) 50 ng/mL [absorbance (Abs)] | 0.231 | 0.477 | 0.809 | 1.254 | 1.498 | 1.989 |
| ΔOD [absorbance (Abs)] | 0.187 | 0.338 | 0.596 | 0.790 | 0.901 | 0.925 |

In addition, concerning the above combinations of the partial peptides (c) and (e) and the recombinant protein of full-length prostasin with the POD-labeled competitive substances thereof, for which no competitive reaction had been observed, reactions were carried out with the use of plates onto which the affinity-purified antibodies (c) and (e) obtained in Example 3 and a commercially available anti-prostasin mouse monoclonal antibody (BD Biosciences, catalog No. 612173) had been immobilized. In such reactions, varying concentrations of partial peptides and the recombinant protein of the full-length prostasin and varying concentrations of the above-prepared POD-labeled partial peptides and the POD-labeled recombinant protein of full-length prostasin were added. However, no competitive reaction was observed. The results obtained when varying concentrations (0, 5, 10, 25, 50, and 100 ng/mL) of the unlabeled partial peptides (c) and (e) and the unlabeled recombinant protein of full-length prostasin were added in the presence of the predetermined levels (the concentrations were 0.35, 0.30, and 6.4 μg/mL, respectively) of the POD-labeled partial peptides (c) and (e) and the POD-labeled recombinant protein of full-length prostasin, are shown in the following Table 2 and FIGS. 3 to 5.

Figure 3:
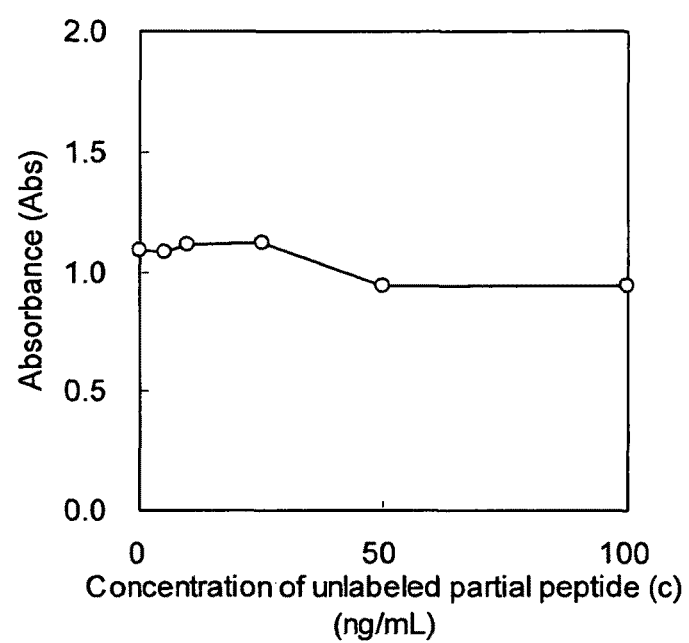
FIG. 3 shows a calibration curve obtained by a competitive immunoassay using POD-labeled partial peptide (c) and affinity-purified antibody (c).
Figure 4:
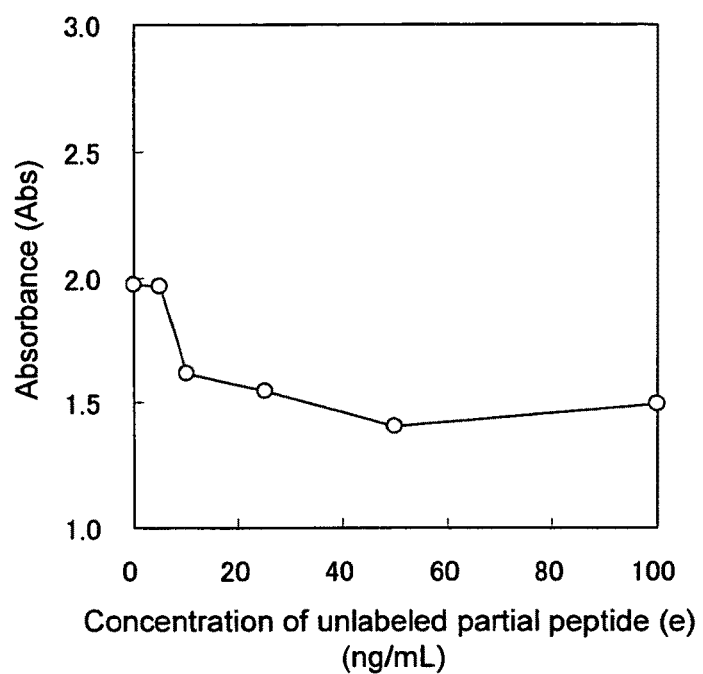
FIG. 4 shows a calibration curve obtained by a competitive immunoassay using POD-labeled partial peptide (e) and affinity-purified antibody (e).
Figure 5:
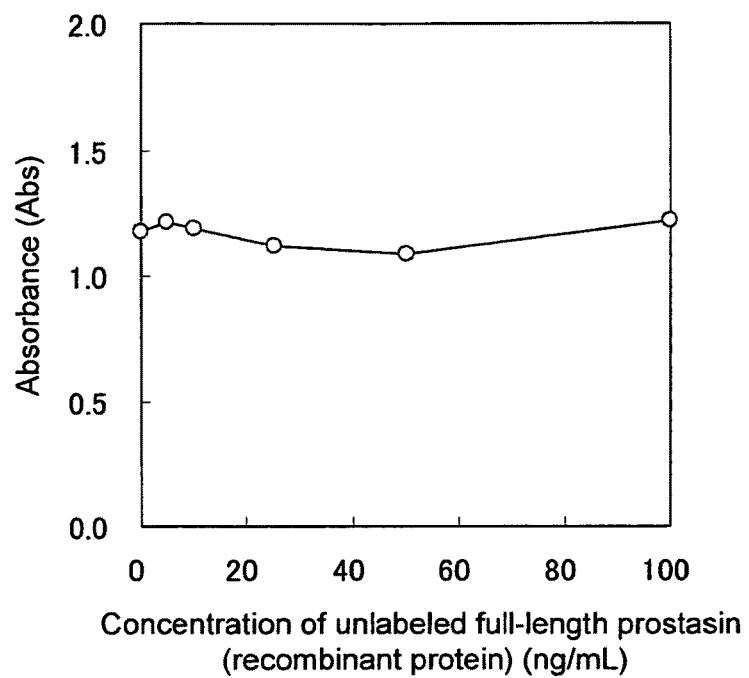
FIG. 5 shows a calibration curve obtained by a competitive immunoassay using a POD-labeled full-length prostasin recombinant protein and a commercially available anti-prostasin mouse monoclonal antibody.

FIG. 3 shows a calibration curve obtained by a competitive immunoassay using the POD-labeled partial peptide (c) and the affinity-purified antibody (c). FIG. 4 shows a calibration curve obtained by competitive immunoassay using the POD-labeled partial peptide (e) and the affinity-purified antibody (e). FIG. 5 shows a calibration curve obtained by a competitive immunoassay using the POD-labeled recombinant protein of full-length prostasin and the commercially available anti-prostasin mouse monoclonal antibody.

TABLE 2

| | Unlabeled partial peptide (protein) concentration [ng/mL] | | | | | |
|---|---|---|---|---|---|---|
| | 0 | 5 | 10 | 25 | 50 | 100 |
| Labeled partial peptide (c) 0.35 μg/mL [absorbance (Abs)] | 1.091 | 1.079 | 1.115 | 1.122 | 0.938 | 0.943 |
| Labeled partial peptide (e) 0.30 μg/mL [absorbance (Abs)] | 1.972 | 1.964 | 1.616 | 1.548 | 1.406 | 1.494 |
| Labeled full-length prostasin (recombinant protein) 6.4 μg/mL [absorbance (Abs)] | 1.178 | 1.213 | 1.192 | 1.122 | 1.087 | 1.220 |

(3) Competitive Immunoassay Using Pod-Labeled Partial Peptide (a)

Figure 2:
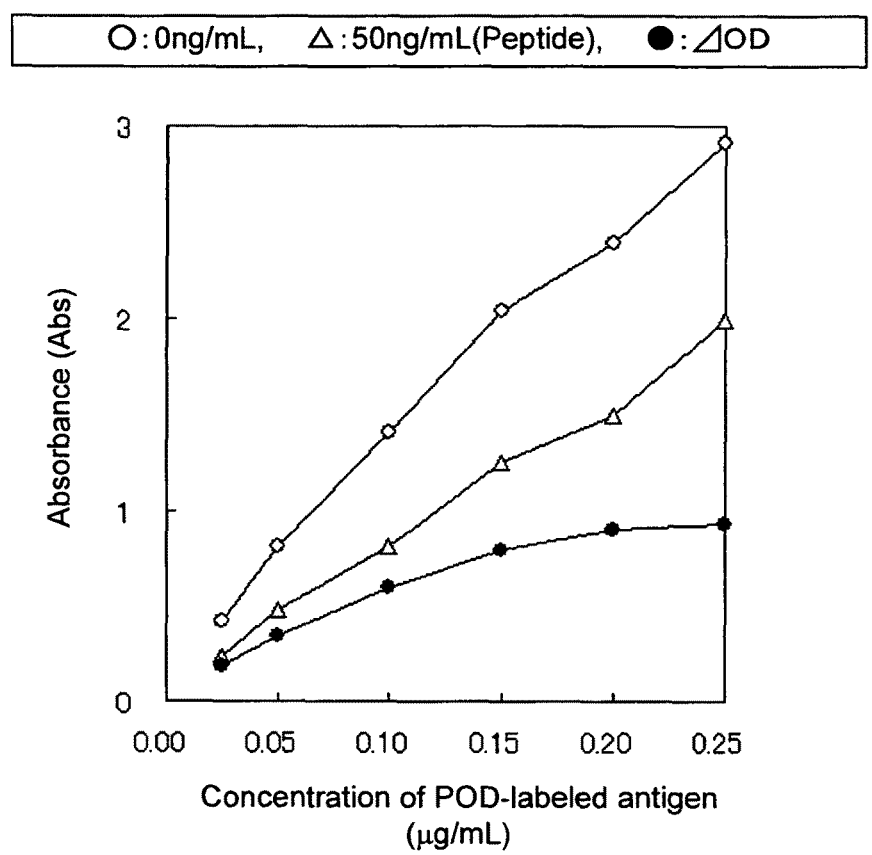
FIG. 2 shows the results of examining the optimum concentration for POD-labeled partial peptide (a).

Based on the above results shown in Table 1 and FIG. 2, the following competitive immunoassay was carried out using the POD-labeled partial peptide (a) with a concentration of 0.20 μg/mL.

Prostasin was measured in 3 negative samples, 1 false positive sample, and 2 positive samples as urine test samples, which had been previously measured by the Western blotting, by the following procedures.

1) The POD-labeled partial peptide (a) (120 μL) was mixed with 120 μL of a standard solution (concentration: 0, 5, 10, 25, 50, or 100 ng/mL) or a test sample.
2) The mixed solution in 1) above was dispensed at 100 μL per well onto an antibody-immobilized plate.
3) Reaction was carried out at room temperature for 1 hour with stirring.
4) Washing was carried out 3 times with 300 μL of 0.1% Tween20/PBS (pH 7.3).
5) TMB coloring solution was dispensed at 100 μL per well.
6) Static reaction was carried out at room temperature for 30 minutes.
7) IN sulfuric acid was dispensed at 100 μL per well.
8) Absorbance was measured at 450 nm/650 nm.

Figure 6:
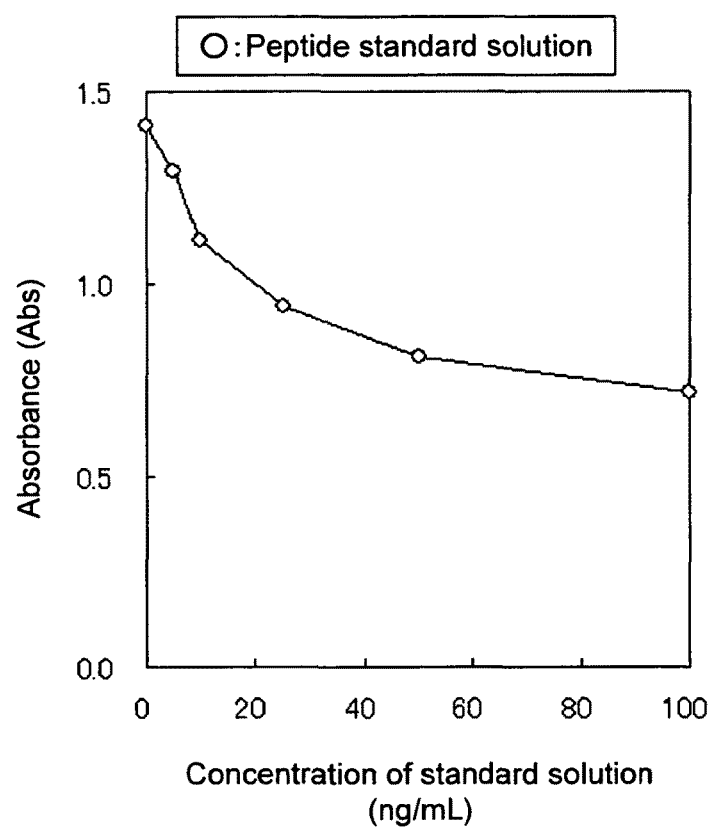
FIG. 6 shows a calibration curve obtained by a competitive immunoassay using POD-labeled partial peptide (a).

The calibration curve obtained above is shown in FIG. 6. Moreover, test samples were similarly examined by the above measurement method and then the prostasin concentrations of the test samples were calculated based on the calibration curve.

The results are shown in Table 3. The concentration in a test sample was converted by multiplying the concentration calculated from the calibration curve by the molecular weight ratio of the full-length prostasin to the partial peptide (a) as a coefficient.

TABLE 3

Measurement results of competitive immunoassay of urine test samples

| Sample No. | 1 | 2 | 3 | 4 | 5 | 6 |
|---|---|---|---|---|---|---|
| Western blotting | – | – | – | ± | ++ | +++ |
| Abs | 1.250 | 1.306 | 1.156 | 0.993 | 0.897 | 0.844 |
| ng/mL | 6.2 | 4.6 | 8.9 | 20.6 | 33.7 | 44.0 |
| ng/mL* | 118 | 86 | 167 | 388 | 635 | 831 |

*Converted in terms of full-length prostasin

As a result, it was confirmed that the results determined by the Western blotting were almost completely consistent and correlated with the measurement results obtained by the competitive immunoassay.

Example 5

In this example, a competitive immunoassay was carried out using an affinity-purified antibody (a).
(1) Preparation of Antibody-Immobilized Plate The affinity-purified antibody (a) (protein concentration: 1 μg/mL) prepared in Example 3, which had been diluted with a carbonate buffer (pH 8.5), was dispensed onto a microtiter plate (Nunc, Maxisorp) at 100 μL per well and then the plate was placed under refrigeration for 16 hours for immobilization. Subsequently, 1% BSA diluted with PBS (pH 7.3) was dispensed at 300 μL per well and then the plate was allowed to stand at room temperature for 2 hours for blocking.

Then, a 2% saccharose solution was dispensed at 300 μL per well and then the plate was allowed to stand at room temperature for 1 hour for blocking. The solutions within the wells were completely discarded and then the wells were dried completely.
(2) Preparation of Biotin-Labeled Antigen A partial peptide (a) corresponding to the affinity-purified antibody (a) obtained in Example 3 was labeled with biotin, so that the partial peptide (a) was prepared as a biotin-labeled antigen.
(3) Competitive Immunoassay Prostasin was measured in 2 negative samples, 2 false positive samples, and 1 positive sample as urine test samples, which had been previously measured by the Western blotting, by the following procedures.

1) The biotin-labeled partial peptide (a) (120 μL) was mixed with 120 μL of a standard solution (concentration: 0, 5, 10, 25, 50, 100, or 200 ng/mL) or a test sample.
2) The mixed solution in 1) above was dispensed at 100 μL per well of an antibody-immobilized plate.
3) Reaction was carried out at room temperature for 1 hour with stirring.
4) Washing was carried out 3 times with 300 μL of 0.1% Tween20/PBS (pH 7.3).
5) Streptavidin-labeled peroxidase (Roche Diagnostics GmbH catalog No. 1089153) was diluted 1:20000 with PBS (pH 7.3) containing 0.4% BlockAce (Dainippon Sumitomo Pharma: catalog No. UK-B80) and 0.1% Tween20, and then the solution was dispensed at 100 μL per well of the antibody-immobilized plate.
6) TMB coloring solution was dispensed at 100 μL per well.
7) Static reaction was carried out at room temperature for 30 minutes.
8) IN sulfuric acid was dispensed at 100 μL per well.
9) Absorbance was measured at 450 nm/650 nm.

Figure 7:
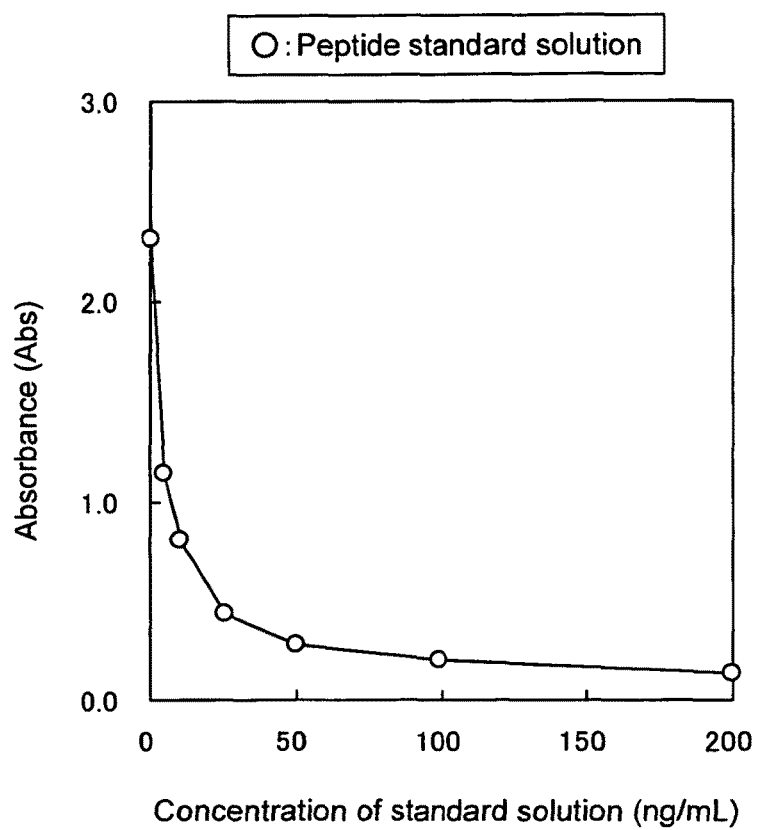
FIG. 7 shows a calibration curve obtained by a competitive immunoassay using biotin-labeled partial peptide (a).

The calibration curve obtained above is shown in FIG. 7. Moreover, test samples were similarly examined by the above measurement method and then the concentrations of prostasin in the test samples were calculated based on the calibration curve.

The results are shown in Table 4. The concentration in a test sample was converted by multiplying a concentration calculated from the calibration curve by the molecular weight ratio of the full-length prostasin to the partial peptide (a) as a coefficient.

TABLE 4

Measurement results of competitive immunoassay of urine test samples

| Sample No. | 1 | 2 | 3 | 4 | 5 |
|---|---|---|---|---|---|
| Western blotting | – | – | ± | ± | + |
| Abs | 1.853 | 1.962 | 1.405 | 1.459 | 0.878 |
| ng/mL | 2.0 | 1.5 | 3.9 | 3.6 | 9.0 |
| ng/mL* | 37.0 | 28.3 | 73.1 | 68.7 | 169.2 |

*Converted in terms of full-length prostasin

As a result, it was confirmed that the results determined by the Western blotting were almost consistent and correlated with the measurement results obtained by the competitive immunoassay.

Example 6

In this example, the within-run reproducibility and the day-to-day reproducibility of prostasin concentrations in 3 specimens (urine samples) were examined by a competitive immunoassay using the affinity-purified antibody (a) and the biotin-labeled partial peptide (a).

(1) Preparation of Antibody-Immobilized Plate and (2) Preparation of Biotin-Labeled Antigen Antibody-immobilized plates and biotin-labeled antigens were prepared in a manner similar to that in Example 5.

(3) Competitive Immunoassay

Prostasin was measured in 3 specimens, A, B, and C (urine samples) by the following procedures.

1) The biotin-labeled partial peptide (a) (50 μL) was mixed with 50 μL of a standard solution (concentration: 0, 5, 10, 25, 50, 100, or 200 ng/mL) or each specimen.

2) The mixed solution in 1) above was dispensed at 100 μL per well of an antibody-immobilized plate.

3) Reaction was carried out at 25° C. for 1 hour with stirring.

4) Washing was carried out 3 times with 300 μL of 0.1% Tween20/PBS (pH 7.3).

5) Streptavidin-labeled peroxidase (Roche Diagnostics GmbH catalog No. 1089153) was diluted 1:20000 with PBS (pH 7.3) containing 0.4% BlockAce (Dainippon Suminomo Pharma: catalog No. UK-B80) and 0.1% Tween20, and then the solution was dispensed at 100 μL per well of the antibody-immobilized plate.

6) Reaction was carried out at 25° C. for 1 hour with stirring.

7) Washing was carried out 3 times with 300 μL of 0.1% Tween20/PBS (pH 7.3).

8) TMB coloring solution was dispensed at 100 μL per well.

9) Static reaction was carried out at 25° C. for 30 minutes.

10) IN sulfuric acid was dispensed at 100 μL per well.

11) Absorbance was measured at 450 nm/650 nm.

Figure 8:
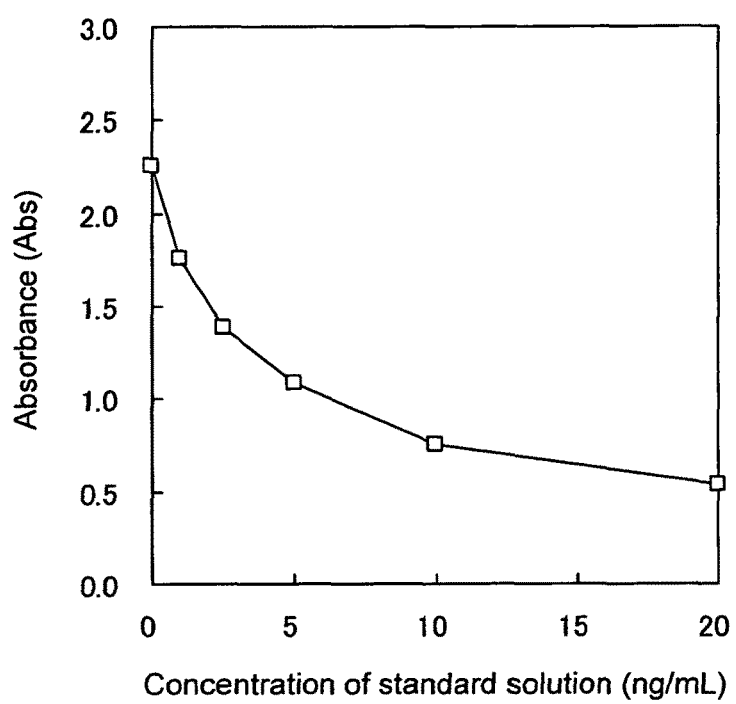
FIG. 8 shows a calibration curve obtained by a competitive immunoassay using biotin-labeled partial peptide (a).

The calibration curve obtained above is shown in FIG. 8. Moreover, specimens A, B, and C were examined by the above measurement method simultaneously or for 1 to 3 days and then the prostasin concentration in each specimen was calculated based on the calibration curve.

The results are shown in Tables 5 and 6. The prostasin concentration in each specimen was converted by multiplying a concentration calculated from the calibration curve by the molecular weight ratio of the full-length prostasin to the partial peptide (a) as a coefficient. Table 5 shows the results of within-run reproducibility, while Table 6 shows the results of day-to-day reproducibility.

TABLE 5

Within-run reproducibility

| No. | Specimen A | Specimen B | (ng/mL) Specimen C |
|---|---|---|---|
| 1 | 2.1 | 2.2 | 4.7 |
| 2 | 1.9 | 1.8 | 3.9 |
| 3 | 1.9 | 1.9 | 4 |
| 4 | 1.9 | 1.9 | 3.9 |
| 5 | 2 | 1.9 | 3.9 |
| 6 | 1.9 | 1.8 | 3.8 |
| 7 | 2 | 1.9 | 4.1 |
| 8 | 1.8 | 1.6 | 4.2 |
| Average | 1.9 | 1.9 | 4.1 |
| SD | 0.099 | 0.16 | 0.28 |
| CV (%) | 5.1 | 8.6 | 6.9 |

TABLE 6

Day-to-day reproducibility

| Day | Specimen A | Specimen B | (ng/mL) Specimen C |
|---|---|---|---|
| 1 | 1.9 | 1.9 | 4.1 |
| 2 | 1.7 | 1.8 | 4.2 |
| 3 | 2.1 | 2 | 4.6 |
| Average | 1.9 | 1.9 | 4.3 |
| SD | 0.182 | 0.092 | 0.265 |
| CV (%) | 9.5 | 4.8 | 6.2 |

As shown in Tables 5 and 6, good results could be obtained such that coefficient of variation (CV) was found to be 10% or lower in both the test concerning within-run reproducibility and the test concerning day-to-day reproducibility.

Example 7

In this example, an enzyme-linked immunosorbent assay (ELISA) was carried out using the recombinant protein of full-length prostasin (used in Example 3) as an antigen, a monoclonal antibody corresponding to the antigen as a primary antibody, and the affinity-purified antibodies (a) and (e) obtained in Example 3, which had been labeled with POD, as labeled secondary antibodies.

(1) Preparation of Antibody-Immobilized Plate

A purified monoclonal antibody [KITAYAMA LABES Co., Ltd.] against the recombinant protein of full-length prostasin used in Example 3 had been customly generated by: preparing a hybridoma strain (2A2C1) by a short-term immunization method using a recombinant protein of full-length prostasin; and then subjecting antibodies obtained from the culture medium to affinity purification using a protein A column. The purified monoclonal antibody was diluted with a phosphate buffer (PBS; 0.15 M NaCl, pH 7.3). Then the solution (protein concentration: 10 μg/mL) was dispensed at 100 μL per well of a microtiter plate (Nunc, Maxisorp) and placed under refrigeration for 16 hours for immobilization. Subsequently, 1% BSA diluted with PBS (pH 7.3) was dispensed at 300 μL per well. The plate was then allowed to stand at room temperature for 2 hours for blocking.

Then, a 20% blocking reagent N101 for immunological assay (produced by NOF CORPORATION: code: S410-03012) diluted with PBS (pH7.3) was dispensed at 300 μL per well. The plate was allowed to stand at room temperature for 2 hours for blocking.

(2) Preparation of POD-Labeled Secondary Antibody

The affinity-purified antibodies (a) and (e) obtained in Example 3 were labeled with peroxidase (POD) and then the affinity-purified antibodies (a) and (e) were prepared as POD-labeled secondary antibodies.

(3) Preparation of Standard Solution

The recombinant protein of full-length prostasin used in Example 3 was diluted with a phosphate buffer (PBS; 0.15 M NaCl, pH 7.3), so as to prepare solutions having different concentrations (0, 25, 50, 100, 200, and 400 ng/mL).

(4) Enzyme-Linked Immunosorbent Assay Method

Measurement was carried out by the following procedures.

1) The standard solution (concentration: 0, 50, 100, 200, or 400 ng/mL) was dispensed at 100 μL per well of an antibody-immobilized plate to carry out reaction at 37° C. for 2 hours.

2) Washing was carried out 3 times with 300 μL of 0.1% Tween20/PBS (pH 7.3).

3) POD-labeled secondary antibodies (protein concentration: 10 μg/mL) of affinity-purified antibodies (a) and (e) were dispensed at 100 μL per well to carry out reaction at 37° C. for 2 hours.

4) Washing was carried out 3 times with 300 μL of 0.1% Tween20/PBS (pH 7.3).

5) TMB coloring solution was dispensed at 100 μL per well.

6) Static reaction was carried out at room temperature for 10 minutes.

7) 1M phosphoric acid was dispensed at 100 μL per well.

8) Absorbance was measured at 450 nm/650 nm.

Figure 9:
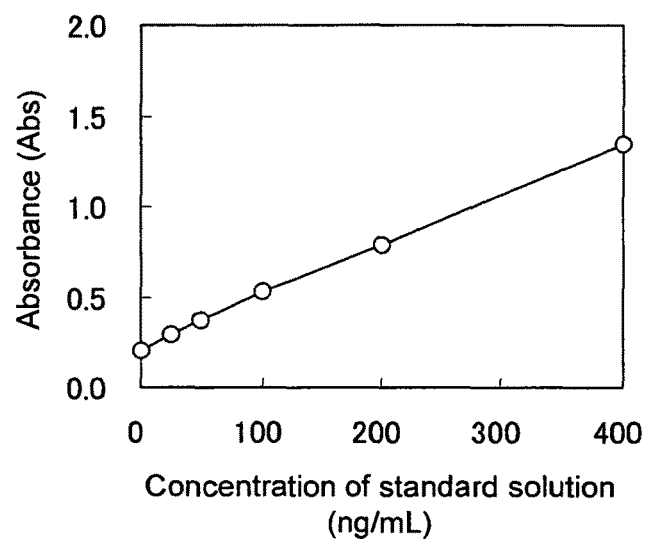
FIG. 9 shows a calibration curve obtained by an enzyme-linked immunosorbent assay using a POD-labeled affinity-purified antibody (a) (obtained by immunization with the partial peptide (a)) as a labeled secondary antibody.
Figure 10:
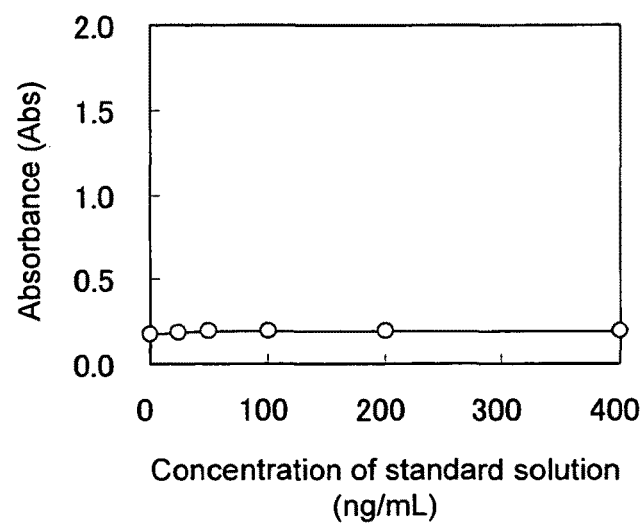
FIG. 10 shows a calibration curve obtained by an enzyme-linked immunosorbent assay using a POD-labeled affinity-purified antibody (e) (obtained by immunization with the partial peptide (e)) as a labeled secondary antibody.

Calibration curves obtained as described above are shown in Table 7 and FIGS. 9 and 10. FIG. 9 shows a calibration curve obtained by an enzyme-linked immunosorbent assay using the affinity-purified antibody (a) (obtained by immunization with the partial peptide (a)) labeled with POD as a labeled secondary antibody. FIG. 10 shows a calibration curve obtained by the enzyme-linked immunosorbent assay using the affinity-purified antibody (e) (obtained by immunization with the partial peptide (e)) labeled with POD as a labeled secondary antibody.

TABLE 7

| | Concentration of standard solution [ng/mL] | | | | | |
|---|---|---|---|---|---|---|
| | 400 | 200 | 100 | 50 | 25 | 0 |
| Affinity-purified antibody (a) (POD-labeled secondary antibody) [absorbance (Abs)] | 1.345 | 0.787 | 0.532 | 0.371 | 0.294 | 0.205 |
| Affinity-purified antibody (e) (POD-labeled secondary antibody) [absorbance (Abs)] | 0.196 | 0.191 | 0.192 | 0.190 | 0.181 | 0.176 |

As a result, in the enzyme-linked immunosorbent assay system using the affinity-purified antibody (a) labeled with POD as a labeled secondary antibody, good reaction was observed in proportional to antigen concentration of the recombinant protein of full-length prostasin and good calibration curve could be obtained. However, in the enzyme-linked immunosorbent assay system using the affinity-purified antibody (e) labeled with POD as a labeled secondary antibody, good reactivity proportional to the antigen concentration of the recombinant protein of full-length prostasin could not be obtained.

Example 8

In this example, with the use of the affinity-purified antibodies (a), (c), and (e) obtained in Example 3, affinity-purified antibodies (b) and (d) obtained by the method similar to that in Example 3, and a commercially available anti-prostasin mouse monoclonal antibody (BD Biosciences, catalog No. 612173), competitive reaction was carried out by the radioimmunoassay (RIA) using a combination of the unlabeled partial peptides (a) to (e) and a recombinant protein of full-length prostasin (however, expressed and purified using silkworm as a host) with the radioisotope (125I)-labeled products thereof or a combination of unlabeled partial peptides (a) to (e) and the radioisotope (125I)-labeled recombinant protein of full-length prostasin.

Measurement was carried out by the following procedures.

1) 1% BSA/PBS (not containing potassium) (300 μL), 100 μL of an affinity-purified antibody (or a commercially available anti-prostasin mouse monoclonal antibody) (containing 1% NRS (normal rabbit serum)) as a primary antibody, and 200 μL of a standard solution (unlabeled partial peptide or recombinant protein of full-length prostasin; concentration: 3.9, 7.8, 15.6, 31.3, or 62.5 μg/mL) were dispensed in this order and then finally 100 μL of a radioisotope (125I)-labeled product was dispensed. The solutions were vortexed shortly for mixing.

2) Incubation was carried out for 16 to 24 hours.

3) A secondary antibody (200 μL, anti-rabbit IgG goat serum (containing approximately 3.2% PEG)) against an affinity-purified antibody (or a commercially available anti-prostasin mouse monoclonal antibody) was dispensed. The solution was vortexed and then incubated overnight.

4) A sample tube was centrifuged at 3500 rpm at 4° C. to 6° C. for 45 to 90 minutes.

5) After centrifugation, the supernatant was aspirated using an aspirator.

6) Gamma ray (125I) was measured using a gamma counter (ALOKA γ system ARC5000).

As a result, competitive reaction was observed when the affinity-purified antibody (a) (obtained using the partial peptide (a) as an antigen) had been used. No competitive reaction was observed when other affinity-purified antibodies (obtained using other partial peptides as antigens) or the commercially available monoclonal antibody had been used.

Specifically, when the affinity-purified antibody (a) had been used, competitive reaction was observed in all combinations including the combination of the partial peptide (a) with the labeled product thereof, the combination of the partial peptide (a) with the labeled recombinant protein of full-length prostasin, and the combination of the recombinant protein of full-length prostasin with the labeled product thereof. However, when other antibodies or partial peptides had been used, no competitive reaction was observed.

Example 9

In this example, in competitive reaction carried out by the RIA method using the affinity-purified antibody (a) obtained in Example 3 and the radioisotope (125I)-labeled partial peptide (a), prostasin was measured in the patient urine specimens. In addition, a calibration curve was generated based on a competitive reaction curve with respect to the radioisotope (125I)-labeled partial peptide (a) using a recombinant protein of full-length prostasin (expressed in silkworm and then purified) as a standard.

Measurement was carried out according to the measurement procedures described in Example 8, except that the affinity-purified antibody (a) was used as a primary antibody, 200 μL of the urine specimen of each patient was used instead of an unlabeled partial peptide or a recombinant protein of full-length prostasin, and a radioisotope (125I)-labeled partial peptide (a) was used as a labeled product.

Figure 11:
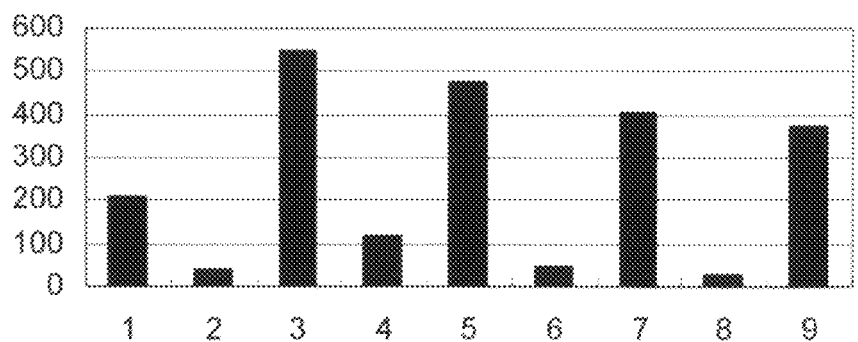
FIG. 11 shows the results of measuring prostasin in the urine specimen of each patient by the RIA method and the results of detecting prostasin in patient urine specimens by Western blotting using a commercially available anti-prostasin mouse monoclonal antibody.
Figure 11:
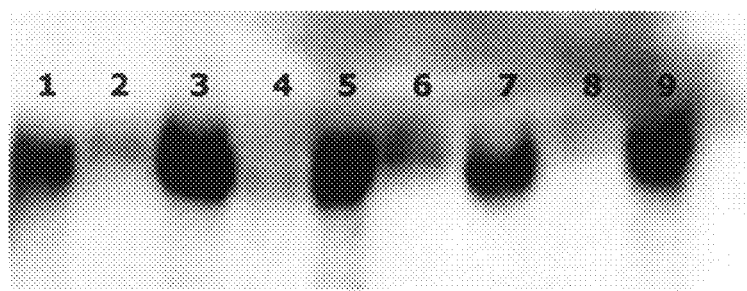
Figure 11:
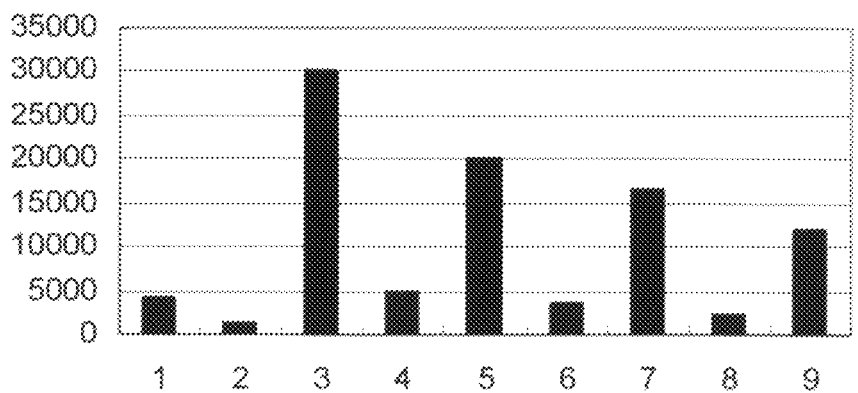

The results are shown in FIG. 11. FIG. 11 shows the results of measuring prostasin in the urine specimen of each patient by the RIA method (A: numerical figures on the longitudinal axis denote prostasin concentrations (ng/mL) in urine) and the results of detecting prostasin in the patient urine specimens by Western blotting using a commercially available anti-prostasin mouse monoclonal antibody (BD Biosciences, catalog No. 612173) (B: the lower graph shows the relative intensities based on the bands obtained by the above Western blotting). In FIG. 11, each No. denotes the number of the urine specimen of each patient.

As shown in FIG. 11, when the urine specimens of 9 patients were measured, the results of measuring prostasin in the urine specimen of each patient by the RIA method were

Example 10

In this example, prostasin concentrations and aldosteron concentrations in patient urine specimens were measured and compared. The patients were those with normal blood pressure (less than 140/90 mmHg) and hypertension patients (140/90 mmHg or higher; A patient under treatment using a drug was considered as a hypertension patient even if the blood pressure was less than 140/90 mmHg). The total number of the patients was 121 (Age: 20-86 years old, Average age: 57.9, Male: 55, and Female: 66).

Prostasin concentrations in the urine specimens of the patients were measured according to Example 9. Meanwhile, aldosteron concentrations in the urine specimens of the patients were measured by the RIA solid phase method.

Figure 12:
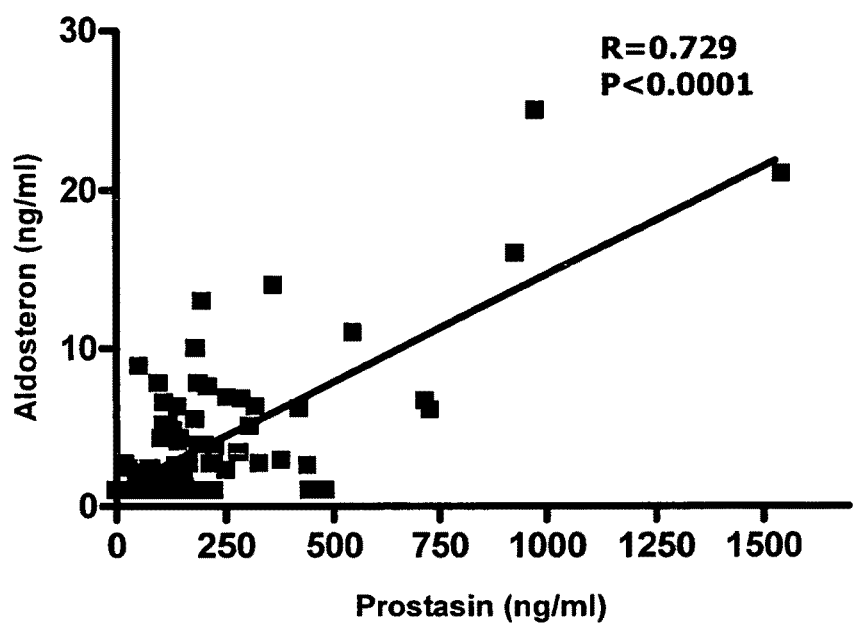
FIG. 12 shows the correlation between prostasin concentrations and aldosteron concentrations in patient urine specimens.

The results are shown in FIG. 12. FIG. 12 shows the correlation between prostasin concentrations and aldosteron concentrations in the patient urine specimens.

As shown in FIG. 12, positive correlation, correlation coefficient of R=0.729 (significance level: P<0.0001), was observed between prostasin concentrations and aldosteron concentrations in the patient urine specimens.

INDUSTRIAL APPLICABILITY

The present invention provides a partial peptide of human prostasin and an anti-prostasin antibody. The partial peptide of the present invention can be used to provide a peptide antigen that has steady quality as an antigen for detection and diagnosis of prostasin and thus can be stably available. Moreover, an antibody having reactivity to the partial peptide of the present invention can be used to analyze, detect, or measure free low-molecular-weight prostasin, high-molecular-weight prostasin binding to inhibitor proteins, and the like in samples under denaturation conditions and non-denaturation conditions. Furthermore, an immunological assay using an antibody that has reactivity to the partial peptide of the present invention makes it possible to provide new data for the wider range of detection of prostasin in various samples and thus to establish a clinical significance.

Furthermore, the partial peptide and the anti-prostasin antibody of the present invention can be used to rapidly, efficiently, and precisely measuring prostasin. Thus, they are useful in diagnosis and the like of prostasin-associated diseases.

All publications, patents, and patent applications cited herein are incorporated herein by reference in their entirety.

SEQUENCE LISTING FREE TEXT

SEQ ID NOS: 1 and 4 to 10: Synthetic peptides

---

The invention claimed is:

1. A peptide consisting of an amino acid sequence that has a deletion, a substitution, or an addition consisting of one to five amino acids with respect to the amino acid sequence shown in SEQ ID NO: 1, and having antigenicity of prostasin.

2. The peptide according to claim 1, wherein said amino acid sequence has a deletion, a substitution or an addition consisting of one to three amino acids with respect to the amino acid sequence shown in SEQ ID NO: 1.

3. A peptide having a carrier protein bound thereto, the peptide being the peptide according to claim 1.

4. A peptide having a label bound thereto, the peptide being the peptide according to claim 1.

5. An antibody, which is prepared using the peptide according to claim 1 as an antigen, wherein the antibody reacts with the peptide and/or specifically binds to a prostasin under denaturation and non-denaturation conditions, and wherein the antibody is a monoclonal antibody.

6. The antibody according to claim 5, wherein a label is bound to the antibody.

7. The antibody according to claim 5, wherein a radioactive label, an enzyme label, or biotin is bound to the antibody.

8. A reagent for an immunological assay for prostasin, comprising the antibody according to claim 5.

9. A diagnostic kit for a prostasin-associated disease, comprising the antibody according to claim 5.

10. A reagent for an immunological assay for prostasin, comprising:
(a) an antibody, which is prepared using the peptide according to claim 1 as an antigen, wherein the antibody reacts with the peptide and/or specifically binds to a prostasin under denaturation and non-denaturation conditions; and
(b) a peptide consisting of the amino acid sequence that has a deletion, a substitution, or an addition consisting of not more than one to five amino acids with respect to the amino acid sequence shown in SEQ ID NO: 1, and having antigenicity of prostasin, which is used as a competitive substance in a competitive immunoassay for prostasin.

11. A method for detecting prostasin in a sample, comprising the steps of:
(a) contacting the antibody according to claim 5 with a sample; and (b) detecting whether or not the antibody binds to prostasin in the sample.

12. The method according to claim 11, wherein the sample is selected from the group consisting of urine, blood, serum, and plasma.

13. The method according to claim 11, wherein the method is for diagnosing a prostasin-associated disease, wherein in the detecting step it is detected whether there is an overexpression or underexpression of prostasin, the overexpression or underexpression of prostasin showing the existence of the disease, and wherein the prostasin-associated disease is selected from the group consisting of hypertension, ovarian cancer, prostate cancer, and breast cancer.

14. A method for detecting prostasin in a sample, comprising the steps of:
(a) contacting an antibody with a sample; and
(b) detecting whether or not the antibody binds to prostasin in the sample,
wherein the antibody is prepared using the peptide according to claim 1 as an antigen,
wherein the antibody reacts with the peptide and/or specifically binds to a prostasin under denaturation and non-denaturation conditions, and
wherein a peptide consisting of the amino acid sequence that has a deletion, a substitution, or an addition consisting of not more than one to five amino acids with respect to the amino acid sequence shown in SEQ ID NO: 1, and having antigenicity of prostasin, which is used as a competitive substance in a competitive immunoassay for prostasin is added as a competitive substance in step (a).

15. A method for detecting prostasin in a sample, comprising the steps of:
(a) contacting an antibody with a sample; and
(b) detecting whether or not the antibody binds to prostasin in the sample,
wherein the antibody is prepared using the peptide according to claim 1 as an antigen,
wherein the antibody reacts with the peptide and/or specifically binds to a prostasin under denaturation and non-denaturation conditions, and
wherein the antibody is bound to a solid phase.

16. A diagnostic method for a prostasin-associated disease in a subject, comprising the steps of:
(a) contacting the antibody according to claim 5 with a sample from the subject;
(b) detecting whether or not the antibody binds to prostasin in the sample; and
(c) determining whether the subject is affected with the disease based on the result of step (b).

17. The diagnostic method of claim 16, wherein the prostasin-associated disease is selected from the group consisting of hypertension, ovarian cancer, prostate cancer, and breast cancer.

18. A peptide having a label bound thereto, the peptide being the peptide consisting of the amino acid sequence shown in SEQ ID NO: 1.

19. A peptide having a carrier protein bound thereto, the peptide being the peptide consisting of the amino acid sequence shown in SEQ ID NO: 1.

20. An antibody, which is prepared using a peptide consisting of the amino acid sequence shown in SEQ ID NO: 1 as an antigen, wherein the antibody reacts with the peptide and/or specifically binds to a prostasin under denaturation and non-denaturation conditions, and wherein the antibody is a monoclonal antibody.

21. The antibody according to claim 20, wherein a label is bound to the antibody.

22. The antibody according to claim 20, wherein a radioactive label, an enzyme label, or biotin is bound to the antibody.

23. A reagent for an immunological assay for prostasin, comprising the antibody according to claim 20.

24. A diagnostic kit for a prostasin-associated disease, comprising the antibody according to claim 20.

25. A reagent for an immunological assay for prostasin, comprising:
(a) an antibody, which is prepared using a peptide consisting of the amino acid sequence shown in SEQ ID NO: 1 as an antigen, wherein the antibody reacts with the peptide and/or specifically binds to a prostasin under denaturation and non-denaturation conditions; and
(b) a peptide consisting of the amino acid sequence shown in SEQ ID NO: 1, which is used as a competitive substance in a competitive immunoassay for prostasin.

26. A method for detecting prostasin in a sample, comprising the steps of:
(a) contacting the antibody according to claim 20 with a sample; and
(b) detecting whether or not the antibody binds to prostasin in the sample.

27. The method according to claim 26, wherein the sample is selected from the group consisting of urine, blood, serum, and plasma.

28. The method according to claim 26, wherein the method is for diagnosing a prostasin-associated disease, wherein in the detecting step it is detected whether there is an overexpression or underexpression of prostasin, the overexpression or underexpression of prostasin showing the existence of the disease, and wherein the prostasin-associated disease is selected from the group consisting of hypertension, ovarian cancer, prostate cancer, and breast cancer.

29. A method for detecting prostasin in a sample, comprising the steps of:
(a) contacting an antibody with a sample; and
(b) detecting whether or not the antibody binds to prostasin in the sample,
wherein the antibody is prepared using a peptide consisting of the amino acid sequence shown in SEQ ID NO: 1 as an antigen,
wherein the antibody reacts with the peptide and/or specifically binds to a prostasin under denaturation and non-denaturation conditions, and
wherein a peptide consisting of the amino acid sequence shown in SEQ ID NO: 1, which is used as a competitive substance in a competitive immunoassay for prostasin, is added as a competitive substance in step (a).

30. A method for detecting prostasin in a sample, comprising the steps of:
(a) contacting an antibody with a sample; and
(b) detecting whether or not the antibody binds to prostasin in the sample,
wherein the antibody is prepared using a peptide consisting of the amino acid sequence shown in SEQ ID NO: 1 as an antigen,
wherein the antibody reacts with the peptide and/or specifically binds to a prostasin under denaturation and non-denaturation conditions, and
wherein the antibody is bound to a solid phase.

31. A diagnostic method for a prostasin-associated disease in a subject, comprising the steps of:
(a) contacting the antibody according to claim 20 with a sample from the subject;
(b) detecting whether or not the antibody binds to prostasin in the sample; and (c) determining whether the subject is affected with the disease based on the result of step (b).

32. The diagnostic method of claim 31, wherein the prostasin-associated disease is selected from the group consisting of hypertension, ovarian cancer, prostate cancer, and breast cancer.

33. A method for producing an antibody against prostasin, comprising the steps of:
- (a) preparing (i) a peptide consisting of the amino acid sequence shown in SEQ ID NO: 1, or (ii) a peptide consisting of an amino acid sequence that has a deletion, a substitution, or an addition consisting of not more than one to five amino acids with respect to the amino acid sequence shown in SEQ ID NO: 1, and having antigenicity of prostasin;
- (b) administering the peptide to an animal; and
- (c) collecting the antibody against the peptide from the animal.

34. A method for producing an antibody against prostasin, comprising the steps of:
- (a) preparing (i) a peptide consisting of the amino acid sequence shown in SEQ ID NO: 1, or (ii) a peptide consisting of an amino acid sequence that has a deletion, a substitution, or an addition consisting of not more than one to five amino acids with respect to the amino acid sequence shown in SEQ ID NO: 1, and having antigenicity of prostasin;
- (b) administering the peptide to an animal;
- (c) collecting antibody-producing cells from the animal;
- (d) fusing the antibody-producing cells with myeloma cells to obtain hybridomas; and
- (e) collecting then antibody against the peptide from the hybridomas.

* * * * *